United States Patent
Hlavinka et al.

(10) Patent No.: US 7,438,679 B2
(45) Date of Patent: Oct. 21, 2008

(54) APPARATUS AND METHOD FOR SEPARATING VOLUMES OF A COMPOSITE LIQUID WITH A BALANCING ASSEMBLY

(75) Inventors: Dennis J. Hlavinka, Arvada, CO (US); Eric T. Hansen, Thornton, CO (US)

(73) Assignee: CaridianBCT Biotechnologies, LLC, Lakewood, CO (US)

( * ) Notice: Subject to any disclaimer, the term of this patent is extended or adjusted under 35 U.S.C. 154(b) by 0 days.

(21) Appl. No.: 11/957,946

(22) Filed: Dec. 17, 2007

(65) Prior Publication Data
US 2008/0096749 A1    Apr. 24, 2008

Related U.S. Application Data

(63) Continuation of application No. PCT/US2006/021827, filed on Jun. 5, 2006.

(60) Provisional application No. 60/693,320, filed on Jun. 22, 2005.

(51) Int. Cl.
*B04B 9/14* (2006.01)

(52) U.S. Cl. .............. 494/82; 494/16; 494/30; 494/37

(58) Field of Classification Search ........ 494/1, 494/10, 12, 16–21, 27–30, 33, 37, 45, 82, 494/84; 74/572.4, 573.1, 573.11; 210/85, 210/144; 73/457, 458; 68/23.1, 23.2
See application file for complete search history.

(56) References Cited

U.S. PATENT DOCUMENTS

| | | | |
|---|---|---|---|
| 3,427,896 A * | 2/1969 | Hartman, Jr. ............. | 74/572.4 |
| 3,640,388 A | 2/1972 | Ferrari | |
| 3,718,133 A | 2/1973 | Perry et al. | |
| 3,747,843 A | 7/1973 | Joyce | |
| 3,812,724 A * | 5/1974 | Curtz et al. ............. | 73/458 |
| 3,921,898 A * | 11/1975 | Finkel ............. | 494/26 |
| 3,954,414 A | 5/1976 | Samson, Jr. et al. | |
| 4,091,989 A | 5/1978 | Schlutz | |
| 4,098,456 A | 7/1978 | Bayham | |
| 4,157,781 A * | 6/1979 | Maruyama ............. | 494/7 |
| 4,191,469 A | 3/1980 | Flossdorf et al. | |
| 4,295,386 A * | 10/1981 | Zhivotov ............. | 464/180 |
| 4,296,882 A | 10/1981 | Kobayashi | |
| 4,303,913 A | 12/1981 | Latham, Jr. | |

(Continued)

FOREIGN PATENT DOCUMENTS

DE      20015684      2/2001

(Continued)

OTHER PUBLICATIONS

PCT/US0621827 International Search Report and Written Opinion, Oct. 20, 2006.

*Primary Examiner*—Charles E Cooley
(74) *Attorney, Agent, or Firm*—Edna M. O'Connor; Laura B. Arciniegas; John R. Merkling

(57) ABSTRACT

Apparatus and method for balancing a centrifuge having interconnected hydraulic chambers in containers on a rotor, each container being adapted to receive a composite fluid, comprising transferring, by the rotation of the rotor, hydraulic liquid from a source to the interconnected hydraulic chambers to balance the centrifuge.

12 Claims, 14 Drawing Sheets

U.S. PATENT DOCUMENTS

| | | | |
|---|---|---|---|
| 4,412,831 A | 11/1983 | Avery et al. | |
| 4,767,397 A | 8/1988 | Hohenberg et al. | |
| 4,781,687 A | 11/1988 | Wall | |
| 4,842,576 A | 6/1989 | Lysaght et al. | |
| 4,850,952 A | 7/1989 | Figdor et al. | |
| 4,887,411 A | 12/1989 | Rondeau et al. | |
| 4,911,703 A | 3/1990 | Lysaght et al. | |
| 4,919,646 A * | 4/1990 | Perdriat | 494/1 |
| 4,939,081 A | 7/1990 | Figdor et al. | |
| 5,651,766 A | 7/1997 | Kingsley et al. | |
| 5,715,731 A * | 2/1998 | Koch | 74/572.4 |
| 5,728,060 A | 3/1998 | Kingsley et al. | |
| 5,733,253 A | 3/1998 | Headley et al. | |
| 5,770,069 A | 6/1998 | Meryman | |
| 5,779,660 A | 7/1998 | Kingsley et al. | |
| 5,788,621 A | 8/1998 | Eady | |
| 5,853,382 A | 12/1998 | Kingsley et al. | |
| 5,885,239 A | 3/1999 | Headley et al. | |
| 6,007,509 A | 12/1999 | Kingsley et al. | |
| 6,019,742 A | 2/2000 | Headley et al. | |
| 6,027,441 A | 2/2000 | Cantu et al. | |
| 6,039,711 A | 3/2000 | Headley et al. | |
| 6,060,022 A | 5/2000 | Pang et al. | |
| 6,074,335 A | 6/2000 | Headley et al. | |
| 6,099,491 A | 8/2000 | Headley et al. | |
| 6,102,883 A | 8/2000 | Kingsley et al. | |
| 6,168,561 B1 | 1/2001 | Cantu et al. | |
| 6,251,291 B1 | 6/2001 | Lamphere et al. | |
| 6,254,784 B1 | 7/2001 | Nayak et al. | |
| 6,261,217 B1 | 7/2001 | Unger et al. | |
| 6,296,602 B1 | 10/2001 | Headley et al. | |
| 6,315,706 B1 | 11/2001 | Unger et al. | |
| 6,348,031 B1 | 2/2002 | Unger et al. | |
| 6,348,156 B1 | 2/2002 | Vishnoi et al. | |
| 6,398,760 B1 | 6/2002 | Danby | |
| 6,413,200 B1 | 7/2002 | Jorgensen et al. | |
| 6,524,231 B1 | 2/2003 | Westberg et al. | |
| 6,582,349 B1 | 6/2003 | Cantu et al. | |
| 6,585,499 B2 | 7/2003 | Nguyen et al. | |
| 6,602,179 B1 | 8/2003 | Headley et al. | |
| 6,605,223 B2 | 8/2003 | Jorgensen et al. | |
| 6,652,475 B1 | 11/2003 | Sahines et al. | |
| 6,666,665 B1 | 12/2003 | Nguyen et al. | |
| 6,733,433 B1 | 5/2004 | Fell | |
| 6,827,863 B2 | 12/2004 | Doleck et al. | |
| 6,852,074 B1 * | 2/2005 | Jorgenson et al. | 494/13 |
| 2002/0082153 A1 | 6/2002 | Jorgensen et al. | |
| 2003/0191005 A1 | 10/2003 | Coelho et al. | |
| 2003/0195104 A1 | 10/2003 | Hlavinka et al. | |
| 2003/0211927 A1 | 11/2003 | Cantu et al. | |
| 2004/0104182 A1 | 6/2004 | Holmes et al. | |
| 2008/0090714 A1 * | 4/2008 | Hudock et al. | |
| 2008/0096749 A1 * | 4/2008 | Hlavinka et al. | |

FOREIGN PATENT DOCUMENTS

| | | |
|---|---|---|
| EP | 0014093 | 5/1983 |
| EP | 0350495 | 8/1992 |
| EP | 0536594 | 4/1993 |
| EP | 0235160 | 6/1994 |
| EP | 0587257 | 6/1998 |
| EP | 0578086 | 8/2001 |
| EP | 1208856 | 5/2002 |
| NL | 1008210 | 2/1998 |
| WO | WO92/00145 | 1/1992 |
| WO | WO00/54823 | 9/2000 |
| WO | WO00/54824 | 9/2000 |
| WO | WO03/26802 | 4/2003 |
| WO | WO03/089027 | 10/2003 |
| WO | WO 2006054828 A1 * | 5/2006 |
| WO | WO2007/001754 | 1/2007 |

* cited by examiner

APPARATUS AND METHOD FOR SEPARATING VOLUMES OF A COMPOSITE LIQUID WITH A BALANCING ASSEMBLY

CROSS REFERENCE TO RELATED APPLICATIONS

This application is a continuation of International Application No. PCT/US2006/021827 filed Jun. 5, 2006 which claims the benefit of U.S. provisional Application No. 60/693,320 filed Jun. 22, 2005.

FIELD OF THE INVENTION

The present invention relates to apparatus and a method for balancing a centrifuge.

BACKGROUND

The apparatus and method of the invention are particularly appropriate for the separation of biological fluids comprising an aqueous component and one or more cellular components. For example, potential uses of the invention include: extracting a plasma component and a cellular component (including platelets, white blood cells, and red blood cells) from a volume of whole blood, the cellular component being subsequently filtered so as to remove platelets and white blood cells from the red blood cells; extracting a plasma component, in which a substantial amount of platelets is suspended, and a red blood cell component from a volume of whole blood, the white blood cells being subsequently removed by filtration from the platelet component and the red blood cell component; extracting a plasma component, a platelet component, and a red blood cell component from a volume of whole blood, the white blood cells being subsequently removed by filtration from the platelet component and the red blood cell component.

An apparatus for processing blood components is known from document WO 03/089027. This apparatus comprises a centrifuge adapted to cooperate with an annular separation bag connected to at least one product bag, e.g. a platelet component bag.

The centrifuge includes a rotor having a turntable for supporting the separation bag, and a central compartment for containing the product bag connected to the separation bag; and a squeezing system for squeezing the separation bag and causing the transfer of a separated component (e.g. platelets suspended in plasma) from the separation bag into the product bag.

With this apparatus, a single discrete volume of blood is processed at once.

An object of the present invention is to design a separation apparatus that can process at once at least two discrete volumes of a composite liquid, in particular discrete volumes that may or may not be the same, and with the proportions of the various components of the composite liquid that may vary from one discrete volume to another one. The object of the invention is further to maintain the centrifuge that is part of the separation apparatus in balance even when the discrete volumes and/or the components are not the same.

One aspect of the invention relates to a balancing assembly for a centrifuge having a rotor and more than one container on the rotor wherein each container is adapted to receive a composite fluid. The balancing assembly comprises a source of hydraulic liquid; a rotor duct in the rotor directly connected to the source of hydraulic liquid; an hydraulic chamber in each container on the rotor wherein the hydraulic chambers are interconnected and are connected to the rotor duct; a motor for rotating the rotor wherein rotation of the rotor causes hydraulic liquid to be transferred from the source to the interconnected hydraulic chambers to balance any unbalance in the rotor due to differences.

Another aspect of the invention relates to a method of balancing a centrifuge having a rotor and more than one containers on the rotor wherein each container contains a hydraulic chamber adapted to receive a composite fluid. The method comprises interconnecting the hydraulic chambers; rotating the rotor and the containers on the rotor; transferring a volume of hydraulic liquid into the interconnected hydraulic chambers comprising connecting a source of hydraulic liquid to the interconnected hydraulic chambers, and distributing by the rotation of the rotor the hydraulic liquid from the source to the interconnected hydraulic chambers.

DESCRIPTION OF THE EMBODIMENTS

For the sake of clarity, the invention will be described with respect to a specific use, namely the separation of whole blood into at least two components, in particular into a plasma component and a red blood cell component, or into a plasma component, a platelet component and a red blood cell component. The discrete volume mentioned hereunder will typically be the volume of a blood donation. The volume of a blood donation may vary from one donor to another one (450 ml plus or minus 10%). It is also recalled that the proportion of the components of blood usually varies from one donor to another one, in particular the hematocrit, which is the ratio of the volume of the red blood cells to the volume of the sample of whole blood considered. In other words the density of blood may slightly vary for one donor to another one. It should be understood however that this specific use is exemplary only.

Figure 1:
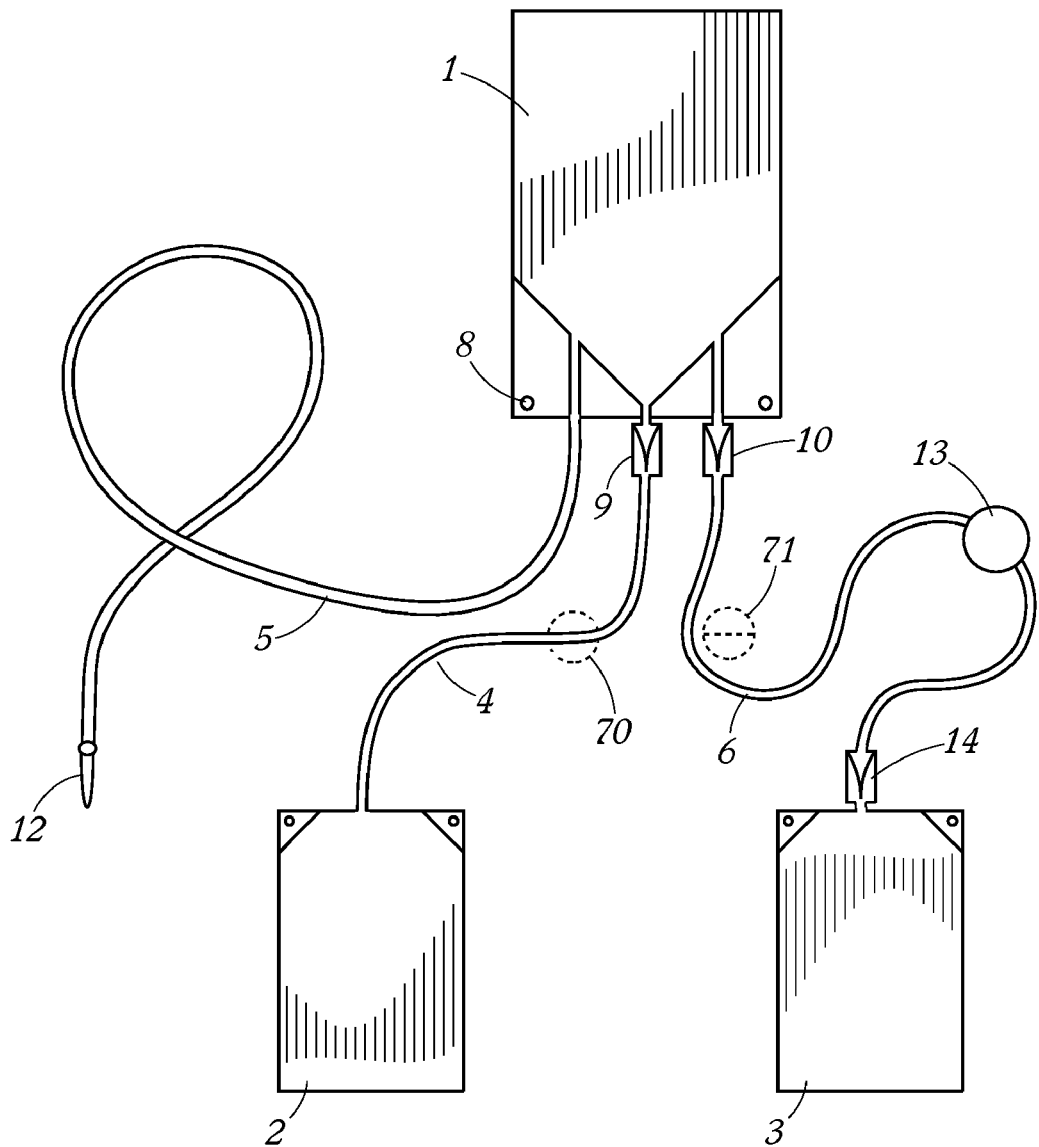
FIG. 1 is a schematic view of a first set of bags designed for cooperating with a separation apparatus.

FIG. 1 shows an example of a set of bags adapted to the separation of a composite liquid (e.g. whole blood) into a first component (e.g. a plasma component containing or not a substantial amount of suspended platelets) and a second component (e.g. a blood cell component). This bag set comprises a flexible separation bag 1 and two flexible satellite bags 2, 3 connected thereto.

When the composite liquid is whole blood, the separation bag 1 has two purposes, and is successively used as a collection bag and as a separation bag. It is intended for initially receiving a discrete volume of whole blood from a donor (usually about 450 ml) and to be used later as a separation chamber in a separation apparatus. The separation bag 1 is flat and generally rectangular. It is made of two rectangular sheets of plastic material that are welded together so as to define therebetween an interior space having a main rectangular portion connected to a triangular top downstream portion. A first tube 4 is connected to the tip of the triangular portion, and second and third tubes 5, 6 are connected to either lateral edges of the triangular portion, respectively. The proximal ends of the three tubes 4, 5, 6 are embedded between the two sheets of plastic material so as to be parallel. The separation bag 1 further comprises a hole 8 in each of its corners that are adjacent to the three tubes 4, 5, 6. The holes 8 are used to secure the separation bag to a separation cell, as will be described later.

The separation bag initially contains a volume of anticoagulant solution (typically about 63 ml of a solution of citrate phosphate dextrose for a blood donation of about 450 ml), and the first and third tubes 4, 6 are fitted at their proximal end with a breakable stopper 9, 10 respectively, blocking a liquid flow therethrough.

The second tube 5 is a collection tube having a needle 12 connected to its distal end. At the beginning of a blood donation, the needle 12 is inserted in the vein of a donor and blood flows into the collection (separation) bag 1. After a desired volume of blood has been collected in the collection (separation) bag 1, the collection tube 5 is sealed and cut.

The first satellite bag 2 is intended for receiving a plasma component. It is flat and substantially rectangular. It is connected to the distal end of the first tube 4.

The second satellite bag 3 is intended for receiving a red blood cell component. It is flat and substantially rectangular. It is connected to the distal end of the third tube 6. The third tube 6 comprises two segments respectively connected to the inlet and the outlet of a leuko-reduction filter 13. The second satellite bag 3 contains a volume of storage solution for red blood cells, and the third tube 6 is fitted at its distal end with a breakable stopper 14 blocking a liquid flow therethrough.

Figure 2:
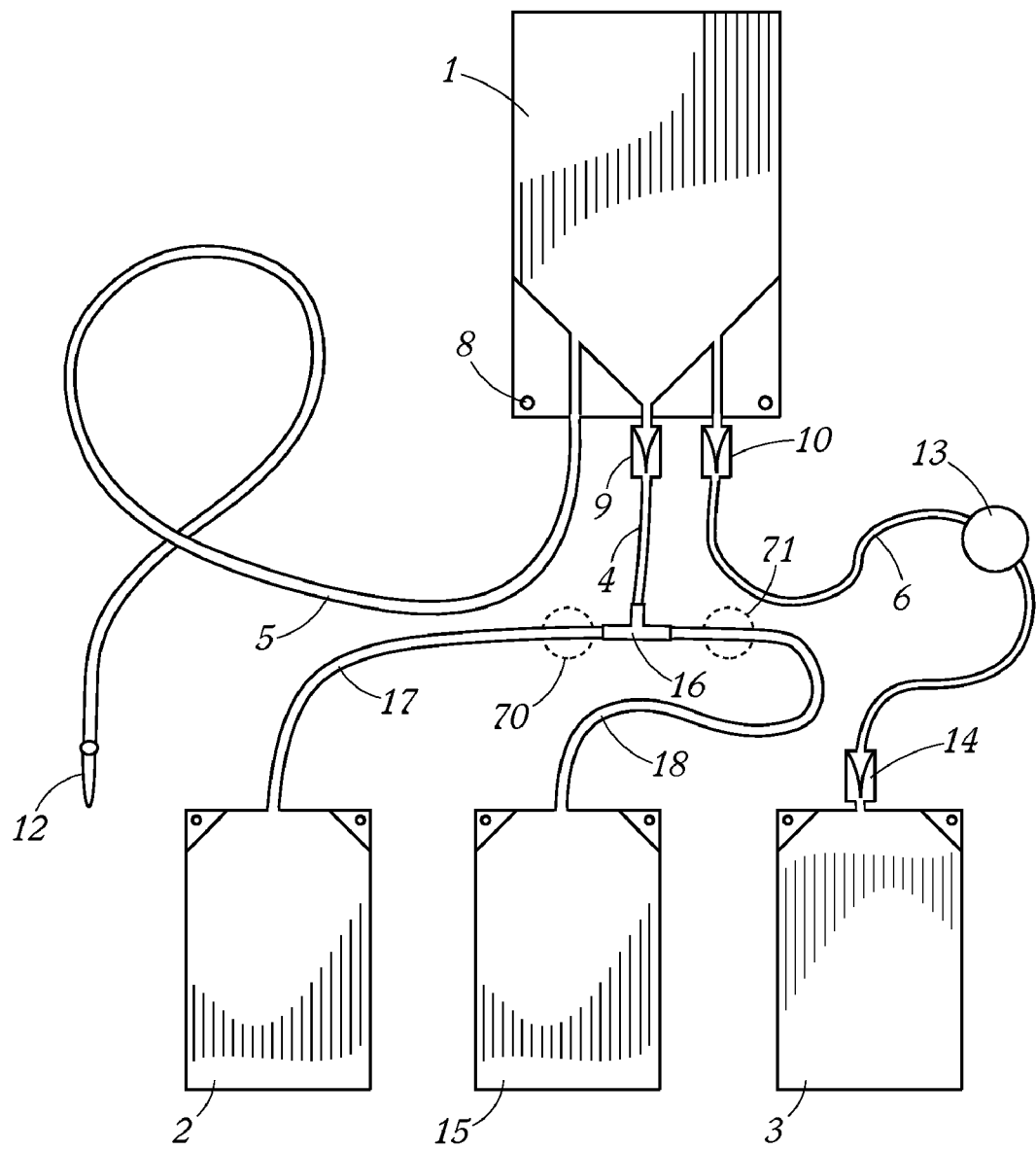
FIG. 2 is a schematic view of a second set of bags designed for cooperating with a separation apparatus.

FIG. 2 shows an example of a set of bags adapted to the separation of a composite liquid (e.g. whole blood) into a first component (e.g. a plasma component), an intermediate component (e.g. a platelet component), and a second component (e.g. a red blood cell component). This bag set comprises a flexible separation bag 1 and three flexible satellite bags 2, 3, 15 connected thereto.

This second set of bags differs from the set of bags of FIG. 1 in that it comprises a third satellite bag 15, which is intended to receive a platelet component, and a T-shaped three-way connector 16 having its leg connected by the first tube 4 to the separation bag 1, a first arm connected by a fourth tube 17 to the first satellite bag 2 (plasma component bag), and a second arm connected by a fifth tube 18 to the third satellite bag 15 (platelet component bag). Like the first and second satellite bags 2, 3, the third satellite bag 15 is flat and substantially rectangular.

Figure 3A:
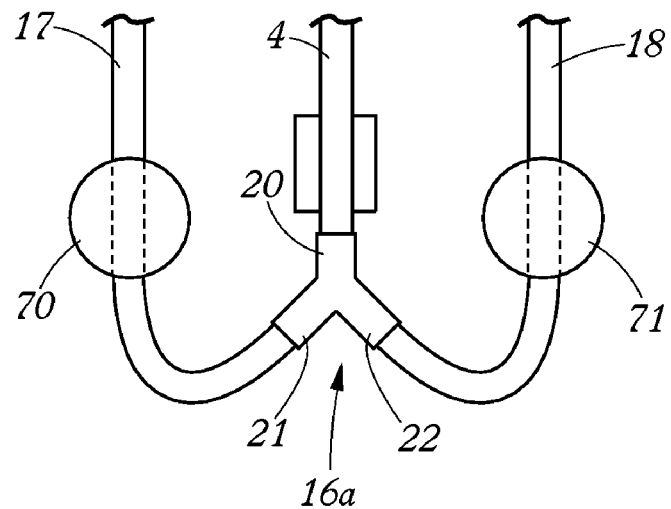
FIGS. 3*a*, 3*b* are schematic views of two variants of a detail of the set of bags of FIG. 2.
Figure 3B:
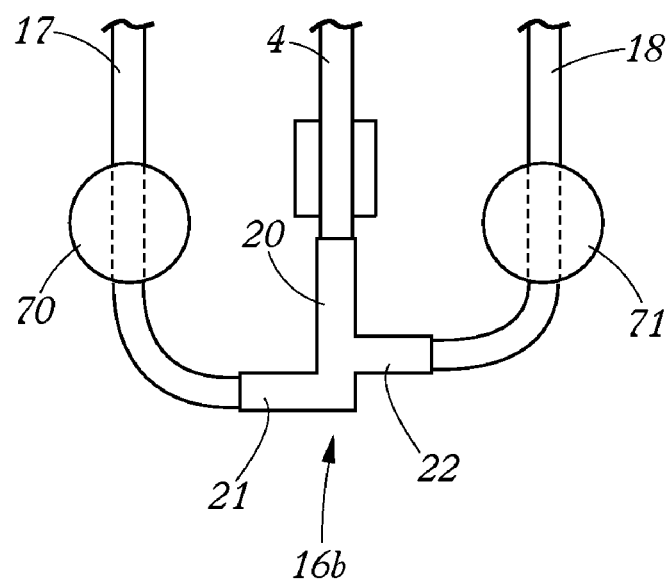

FIGS. 3a, 3b show two variants of the T-shaped three-way connector 16 of the bag set of FIG. 2.

The three-way connector 16a shown in FIG. 3a has the shape of a regular three-point star having a first outlet channel 21 and a second outlet channel 22 that are connected to an inlet channel 20 at an angle of about 120 degrees.

The three-way connector 16b shown in FIG. 3b, defines a first outlet channel 21 and a second outlet channel 22 that are perpendicularly connected to an inlet channel 20 and are offset along the inlet channel 20 so that the first outlet channel 21 is further than the second outlet channel 22 from the end of the inlet channel 20 that is connected to the first tube 4.

The three-way connectors 16, 16a, 16b are arranged such that when the separation bag of FIG. 2 (or any of its variants represented in FIG. 3a, 3b) is mounted in a separation apparatus (to be described in detail below), in which a separation cell for a separation bag 1, a storage container for the satellite bags 2, 3, 15, and a first and second pinch valve members 70, 71 for allowing or stopping a flow of liquid in the fourth and fifth tubes 17, 18 are arranged in this order along a radial direction from a rotation axis of the separation apparatus, with the pinch valve members being the closest to the rotation axis. In this particular configuration, when the fourth and fifth tubes 17, 18 are engaged in the first and second pinch valve members as shown in FIGS. 2, 3a, 3b, then the three-way connector 16, 16b, or a bend in the fourth and fifth tubes 17, 18 in the case of the connector 16a of FIG. 3a, are the closest portion(s) of the whole bag set to the rotation axis. The results of this disposition are that, when the separation apparatus rotates, any air in the bag set will gather in the connector in an area that is the closest to the rotation axis (junction point of the three channels 20, 21, 22 in the connectors shown in FIGS. 2, 3b) or in the bends in the fourth and fifth tube 17, 18 between the connector and the pinch valve members 70, 71 when the connector used is the connector of FIG. 3a. This air buffer between the separation bag and the satellite bag will prevent any undesirable siphoning of contents of a satellite bag into the separation bag under centrifugation forces.

The three-way connector 16b presents a particular interest when the bag set of FIG. 2 is used to separate a plasma component and a platelet component. When the plasma component has been transferred into the first satellite bag 2 and the platelet component has been transferred into the third satellite bag 15, the connector 16b shown in FIG. 3b allow for flushing the second channel 22, which may contain remaining platelets, with a small volume of plasma trapped in the fourth tube 17 between the connector 16b and the first pinch valve member.

FIGS. 4, 5, 6, 8 show a first embodiment of an apparatus for simultaneously separating by centrifugation four discrete volumes of a composite liquid. The apparatus comprises a centrifuge adapted to receive four of either set of bags shown in FIGS. 1 and 2, with the four discrete volumes of a composite liquid contained in the four separation bags; a component transferring means for transferring at least one separated component from each separation bag into a satellite bag connected thereto; a first balancing means for initially balancing the rotor when the weights of the four separation bags are different; and a second balancing means for balancing the rotor when the weights of the separated components transferred into the satellite bags cause an unbalance of the rotor.

The centrifuge comprises a rotor that is supported by a bearing assembly 30 allowing the rotor to rotate around a rotation axis 31. The rotor comprises a cylindrical rotor shaft 32 to which a pulley 33 is connected; a storage means comprising a central cylindrical container 34 for containing satellite bags, which is connected to the rotor shaft 32 at the upper end thereof so that the longitudinal axis of the rotor shaft 32 and the longitudinal axis of the container 34 coincide with the rotation axis 31, and a frusto-conical turntable 35 connected to the upper part of the central container 34 so that its central axis coincides with the rotation axis 31. The frusto-conical turntable 35 flares underneath the opening of the container 34. Four identical separation cells 40 are mounted on the turntable 35 so as to form a symmetrical arrangement with respect to the rotation axis 31.

The centrifuge further comprises a motor 36 coupled to the rotor by a belt 37 engaged in a groove of the pulley 33 so as to rotate the rotor about the rotation axis 31.

Each separation cell 40 comprises a container 41 having the general shape of a rectangular parallelepiped. The separation cells 40 are mounted on the turntable 35 so that their respective median longitudinal axes 42 intersect the rotation axis 31, so that they are located substantially at the same distance from the rotation axis 31, and so that the angles between their median longitudinal axes 42 are substantially the same (i.e. 90 degrees). The exact position of the separation cells 40 on the turntable 35 is adjusted so that the weight on the turntable is equally distributed when the separation cells 40 are empty, i.e. so that the rotor is balanced. It results from the arrangement of the separating cells 40 on the turntable 35 that the separating cells 40 are inclined with respect to the rotation axis 31 of an acute angle equal to the angle of the frustum of a cone that geometrically defines the turntable 35.

Each container 41 comprises a cavity 43 that is so shaped and dimensioned as to loosely accommodate a separation bag 1 full of liquid, of the type shown in FIGS. 1 and 2. The cavity 43 (which will be referred to later also as the "separation compartment") is defined by a bottom wall, that is the farthest to the rotation axis 31, a lower wall that is the closest to the turntable 35, an upper wall opposite to the lower wall, and two lateral walls. The cavity 43 comprises a main part, extending from the bottom wall, which has substantially the shape of a rectangular parallelepiped with rounded angles, and an upper part, which has substantially the shape of a prism having convergent triangular bases. In other words, the upper part of the cavity 43 is defined by two pairs of opposite walls converging towards the central median axis 42 of the cavity 43. One interest of this design is to cause a radial dilatation of the thin layer of a minor component of a composite fluid (e.g. the platelets in whole blood) after separation by centrifugation, and makes it more easily detectable in the upper part of a separation bag. The two pairs of opposite walls of the upper part of the separation cell 40 converge towards three cylindrical parallel channels 44, 45, 46, opening at the top of the container 41, and in which, when a separation bag 1 is set in the container 41, the three tubes 4, 5, 6 extend.

The container 41 also comprises a hinged lateral lid 47 (see FIGS. 8 and 9), which is comprised of an upper portion of the external wall of the container 41, i.e. the wall that is opposite to the turntable 35. The lid 47 is so dimensioned as to allow, when open, an easy loading of a separation bag 1 full of liquid into the separation cell 40. The container 41 comprises a fast locking means (not shown) by which the lid 47 can be locked to the remaining part of the container 41.

The container 41 also comprises a securing means for securing a separation bag 1 within the separation cell 40. The bag securing means comprises two pins 48 protruding on the internal surface of the lid 47, close to the top of separation cell 40, and two corresponding recesses 49 in the upper part of the container 41. The two pins 48 are so spaced apart and dimensioned as to fit into the two holes 8 in the upper corner of a separation bag 1.

The separation apparatus further comprises a component transferring means for transferring at least one separated component from each separation bag into a satellite bag connected thereto. The component transferring means comprises a squeezing system for squeezing the separation bags 1 within the separation compartments 43 and causing the transfer of separated components into satellite bags 2, 3, 15.

The squeezing system comprises a flexible diaphragm 50 that is secured to each container 41 so as to define an expandable chamber 51 in the cavity thereof. More specifically, the diaphragm 50 is dimensioned so as to line the bottom wall of the cavity 43 and a large portion of the lower wall of the cavity 43, which is the closest to the turntable 35.

The squeezing system further comprises a peripheral circular manifold 52 that forms a ring within the turntable 35 extending close to the periphery of the turntable 35. Each expansion chamber 51 is connected to the manifold 52 by a supply channel 53 that extends through the wall of the respective container 41, close to the bottom thereof.

The squeezing system further comprises a hydraulic pumping station 60 for pumping a hydraulic liquid in and out of the expandable chambers 51 within the separation cells 40. The hydraulic liquid is selected so as to have a density slightly higher than the density of the more dense of the components in the composite liquid to be separated (e.g. the red blood cells, when the composite liquid is blood). As a result, during centrifugation, the hydraulic liquid within the expandable chambers 51, whatever the volume thereof, will generally remain in the most external part of the separation cells 40. The pumping station 60 is connected to the expandable chambers 51, through a rotary seal 69, by a duct 56 that extends through the rotor shaft 32, the bottom and lateral wall of the central container 34, and, from the rim of the central container 34, radially through the turntable 35 where it connects to the manifold 52.

The pumping station 60 comprises a piston pump having a piston 61 movable in a hydraulic cylinder 62 fluidly connected via a rotary fluid coupling 63 to the rotor duct 54. The piston 61 is actuated by a stepper motor 64 that moves a lead screw 65 linked to the piston rod. The hydraulic cylinder 62 is also connected to a hydraulic liquid reservoir 66 having an access controlled by a valve 67 for selectively allowing the introduction or the withdrawal of hydraulic liquid into and from a hydraulic circuit including the hydraulic cylinder 62, the rotor duct 56 and the expandable hydraulic chambers 51. A pressure gauge 68 is connected to the hydraulic circuit for measuring the hydraulic pressure therein.

The separation apparatus further comprises four pairs of a first and second pinch valve members 70, 71 that are mounted on the rotor around the opening of the central container 34. Each pair of pinch valve members 70, 71 faces one separation cell 40, with which it is associated. The pinch valve members 70, 71 are designed for selectively blocking or allowing a flow of liquid through a flexible plastic tube, and selectively sealing and cutting a plastic tube. Each pinch valve member 70, 71 comprises an elongated cylindrical body and a head having a groove 72 that is defined by a stationary upper jaw and a lower jaw movable between an open and a closed position. The groove 72 is so dimensioned that one of the tubes 4, 17, 18 of the bag sets shown in FIGS. 1 and 2 can be snuggly engaged therein when the lower jaw is in the open position. The elongated body contains a mechanism for moving the lower jaw and it is connected to a radio frequency generator that supplies the energy necessary for sealing and cutting a plastic tube. The pinch valve members 70, 71 are mounted inside the central container 34, adjacent the interior surface thereof, so that their longitudinal axes are parallel to the rotation axis 31 and their heads protrude above the rim of the container 34. The position of a pair of pinch valve members 70, 71 with respect to a separation bag 1 and the tubes 4, 17, 18 connected thereto when the separation bag 1 rests in the separation cell 40 associated with this pair of pinch valve members 70, 71 is shown in doted lines in FIGS. 1 and 2. Electric power is supplied to the pinch valve members 70, 71 through a slip ring array 38 that is mounted around a lower portion of the rotor shaft 32.

The separation apparatus further comprises four pairs of sensors 73, 74 for monitoring the separation of the various components occurring within each separation bag when the apparatus operates. Each pair of sensors 73, 74 is embedded in the lid 47 of the container 41 of each separation cell 40 along the median longitudinal axis 42 of the container 41, a first sensor 73 being located the farthest and a second sensor 74 being located the closest to the rotation axis 31. When a separation bag 1 rests in the container 41 and the lid 47 is closed, the first sensor 73 (later the bag sensor) faces the upper triangular part of the separation bag 1 and the second sensor 74 (later the tube sensor) faces the proximal end of the first tube 4. The bag sensor 73 is able to detect blood cells in a liquid. The tube sensor 74 is able to detect the presence or absence of liquid in the tube 4 as well as to detect blood cells in a liquid. Each sensor 73, 74 may comprise a photocell including an infrared LED and a photo-detector. Electric power is supplied to the sensors 73, 74 through the slip ring array 38 that is mounted around the lower portion of the rotor shaft 32.

The separation apparatus further comprises a first balancing means for initially balancing the rotor when the weights of the four separation bags 1 contained in the separation cells 40 are different. The first balancing means substantially comprises the same structural elements as the elements of the component transferring means described above, namely: four expandable hydraulic chambers 51 interconnected by a peripheral circular manifold 52, and a hydraulic liquid pumping station 60 for pumping hydraulic liquid into the hydraulic chambers 51 through a rotor duct 56, which is connected to the circular manifold 52. In order to initially balance the rotor, whose four separation cells 40 contain four discrete volumes of a composite liquid that may not have the same weight (because the four volumes may be not equal, and/or the density of the liquid may slightly differ from one volume to the other one), the pumping station 60 is controlled so as to pump into the interconnected hydraulic chambers 51, at the onset of a separation process, a predetermined volume of hydraulic liquid that is so selected as to balance the rotor in the most unbalanced situation. For whole blood, the determination of this balancing volume takes into account the maximum difference in volume between two blood donations, and the maximum difference in hematocrit (i.e. in density) between two blood donations. Under centrifugation forces, the hydraulic liquid will distribute unevenly in the four separation cells 40 depending on the difference in weight of the separation bags 1, and balance the rotor. In order to get an optimal initial balancing, the volume of the cavity 43 of the separation cells 40 should be selected so that the cavities 43, whatever the volume of the separation bags 1 contained therein, are not full after the determined amount of hydraulic liquid has been pumped into the interconnected expansion chambers 51.

Figure 4:
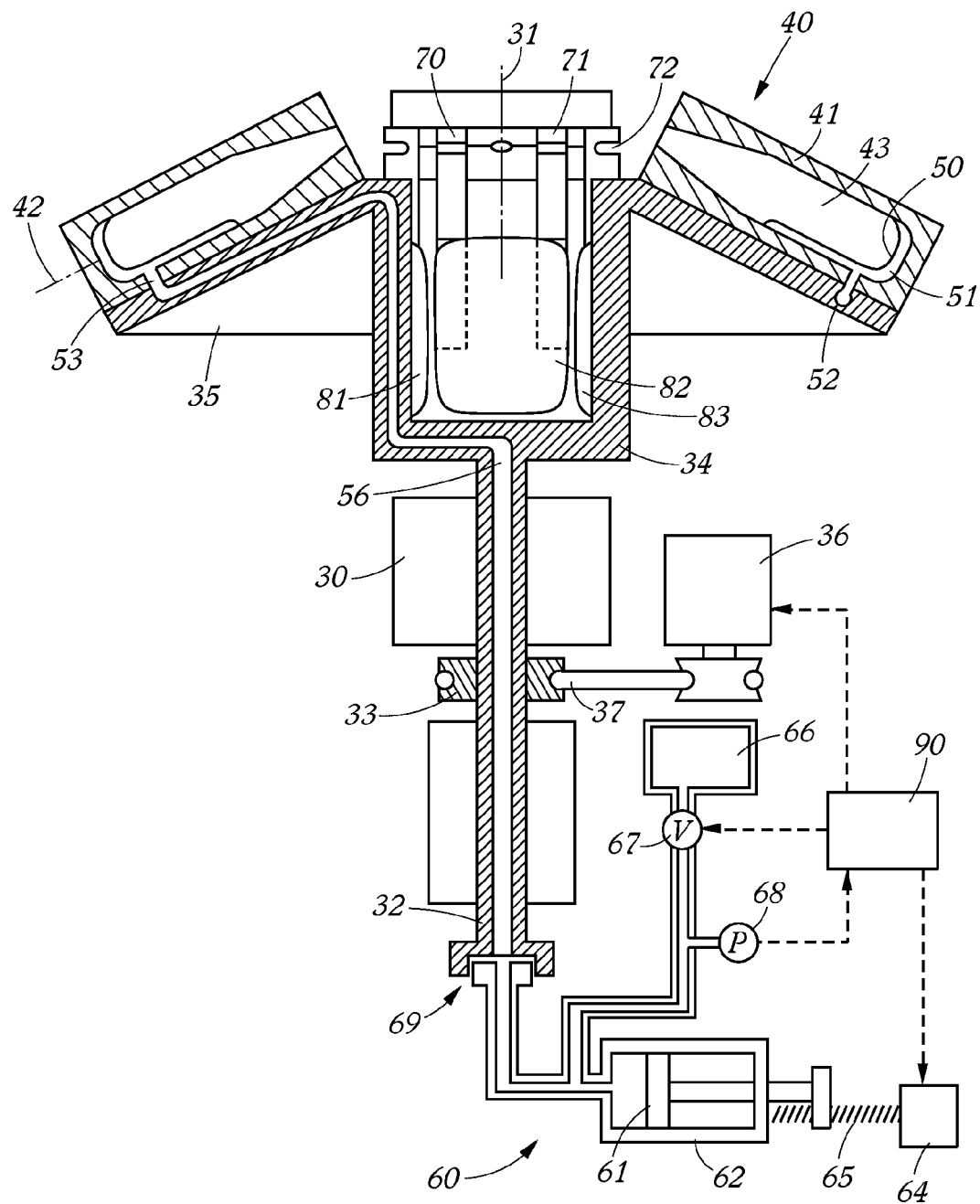
FIG. 4 is a schematic view, partly in cross-section along a diametral plane, of a first embodiment of a separation apparatus.
Figure 5:
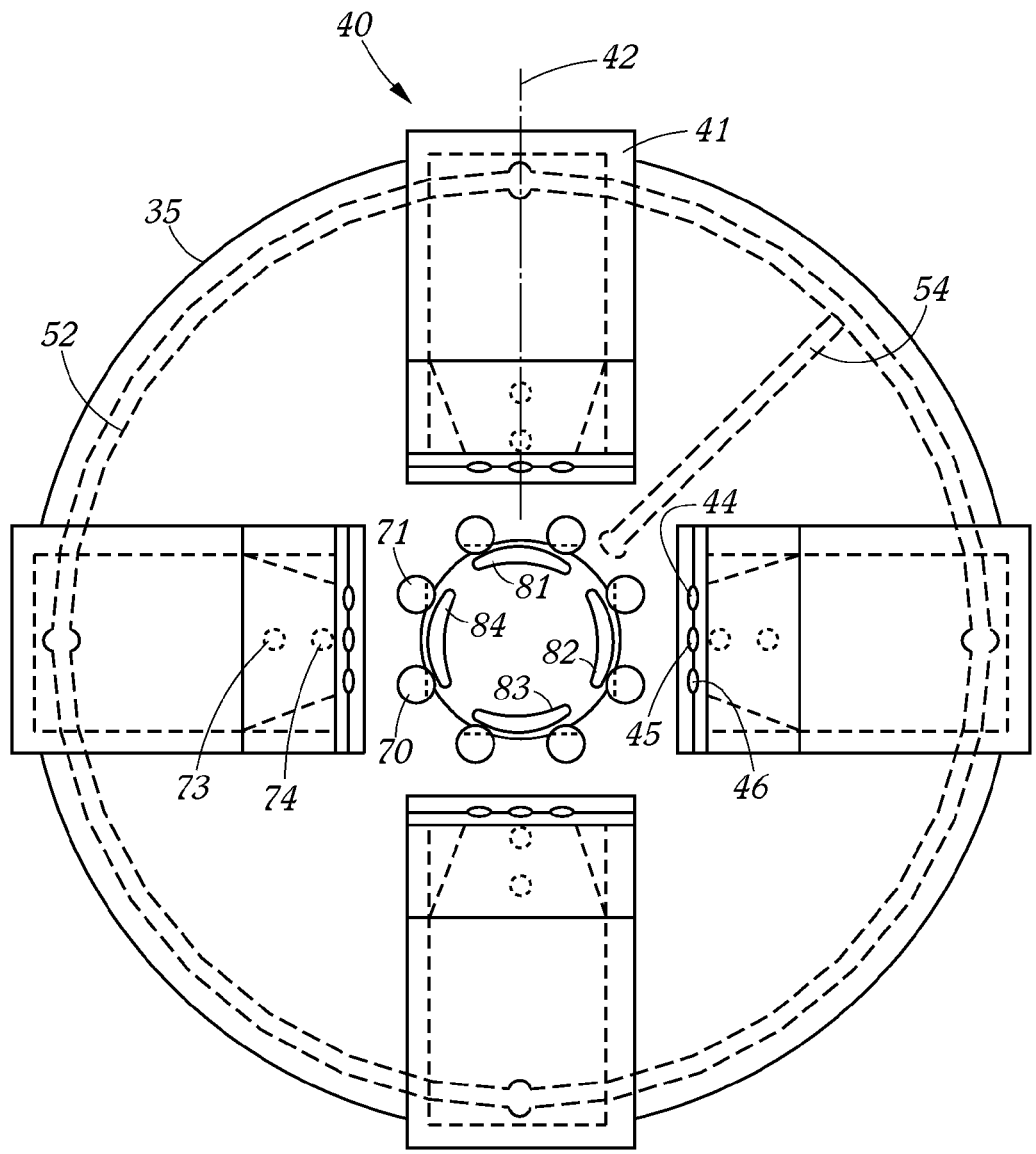
FIG. 5 is a top view of the rotor of the separation apparatus of FIG. 4.
Figure 6:
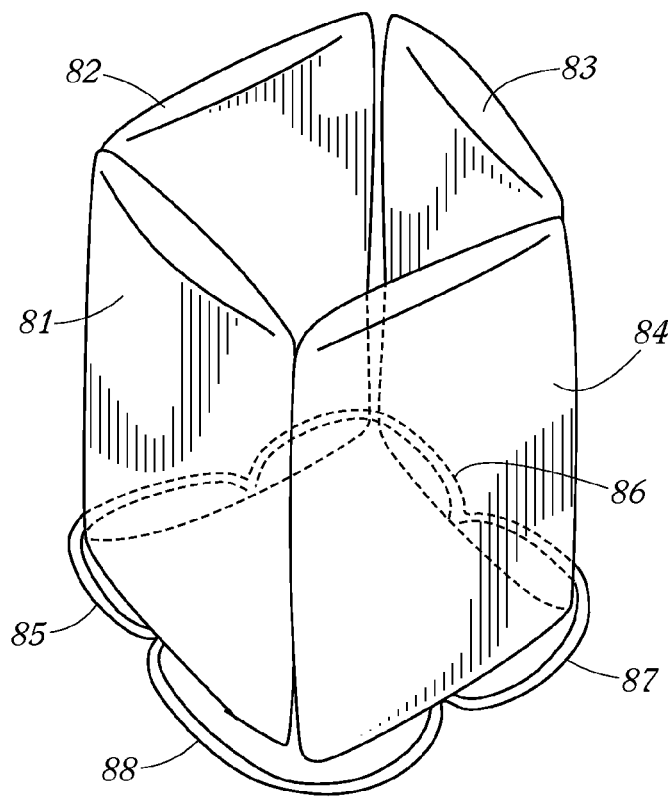
FIG. 6 is a perspective view of a first embodiment of a passive balancing unit for a separation apparatus.

The separation apparatus further comprises a second balancing means, for balancing the rotor when the weights of the components transferred into the satellite bags 2, 3, 15 in the central container 34 are different. For example, when two blood donations have the same hematocrit and different volumes, the volumes of plasma extracted from each donation are different, and the same is true when two blood donations have the same volume and different hematocrit. As shown in FIGS. 4, 5, 6 the second balancing means comprises four flexible rectangular pouches 81, 82, 83, 84 that are interconnected by four tube sections 85, 86, 87, 88, each tube section connecting two adjacent pouches by the bottom thereof. The pouches 81, 82, 83, 84 contain a volume of balancing liquid having a density close to the density of the composite liquid. The volume of balancing liquid is so selected as to balance the rotor in the most unbalanced situation. The four pouches 81, 82, 83, 84 are so dimensioned as to line the inner surface of the central container 34 and to have an internal volume that is larger than the volume of balancing liquid so that the balancing liquid can freely expand in any of the pouches 81, 82, 83, 84. In operation, if, for example, four satellite bags 2 respectively adjacent to the four pouches 81, 82, 83, 84 receive different volumes of a plasma component, the four satellite bags 2 will press unevenly, under centrifugation forces, against the four pouches 81, 82, 83, 84, which will result in the balancing liquid becoming unevenly distributed in the four pouches 81, 82, 83, 84 and compensating for the difference in weight in the satellite bags 2.

The separation apparatus further comprises a controller 90 including a control unit (e.g. a microprocessor) and a memory unit for providing the microprocessor with information and programmed instructions relative to various separation protocols (e.g. a protocol for the separation of a plasma component and a blood cell component, or a protocol for the separation of a plasma component, a platelet component, and a red blood cell component) and to the operation of the apparatus in accordance with such separation protocols. In particular, the microprocessor is programmed for receiving information relative to the centrifugation speed(s) at which the rotor is to be rotated during the various stages of a separation process (e.g. stage of component separation, stage of a plasma component expression, stage of suspension of platelets in a plasma fraction, stage of a platelet component expression, etc), and information relative to the various transfer flow rates at which separated components are to be transferred from the separation bag 1 into the satellite bags 2, 3, 15. The information relative to the various transfer flow rates can be expressed, for example, as hydraulic liquid flow rates in the hydraulic circuit, or as rotation speeds of the stepper motor 64 of the hydraulic pumping station 60. The microprocessor is further programmed for receiving, directly or through the memory, information from the pressure gauge 68 and from the four pairs of photocells 73, 74 and for controlling the centrifuge motor 36, the stepper motor 64 of the pumping station 60, and the four pairs of pinch valve members 70, 71 so as to cause the separation apparatus to operate along a selected separation protocol.

Variants of the first embodiment of the separation apparatus described above are as follows:

Instead of the centralized hydraulic squeezing system described above, a separation apparatus can be fitted with as many independent squeezing means as separation cells 40. An independent squeezing means may be comprised, for example, of a plate that can be moved by any electro-magnetic, electro-mechanical or hydraulic mechanism so as to squeeze a separation bag against a wall of the cavity 43 of the container 41 of a separation cell 40.

Instead of a system of interconnected hydraulic chambers or pouches, the first and/or second balancing means can comprise a ball balancer including a circular cage in which heavy balls can move freely. The circular cage is mounted on the rotor so as to be centered on the rotation axis 31.

Figure 9:
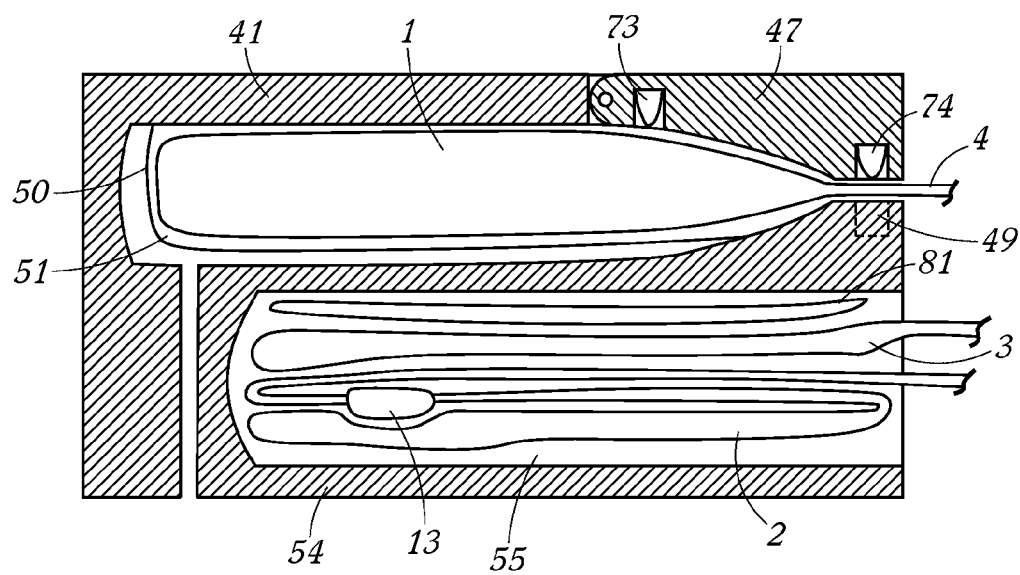
FIG. 9 is schematic view, in cross-section along a radial plane, of an embodiment of a separation cell adjacent to a storage container.

Instead of a central container 34 for containing all the satellite bags 2, 3, 15 connected to the separation bags 1, a separation apparatus can comprise as many satellite bag containers as separation cells. FIG. 9 shows a container arrangement that can be used in such a separation apparatus. The container arrangement of FIG. 9 comprises a separation bag container 41 that is connected to or is made integral with a satellite bag container 54. The satellite bag container 54 comprises a cavity 55 having the shape of a rectangular parallelepiped, which contains a pouch 81 of a balancing assembly as shown in FIG. 6. The separation bag container 41 is superimposed on the satellite bag container 54 so that the openings of both containers are in the same plane, facing the rotation axis 31 when the container arrangement is mounted on a rotor turntable 35.

The second sensors 74 can be embedded in the lids 47 of the containers 41 so as to face an upper part of a separation bag 1 close to the connection thereof to the first tube 4.

The diaphragm 50, instead of being secured to the container 41 so as to line a portion of the lower wall of the cavity 43, can be secured to the container 41 so as to line a portion of the upper wall of the cavity 43.

In each separation cell 40, the hydraulic chamber 51, instead of being defined by a flexible diaphragm 50 lining the bottom wall of the cavity 43 and a large portion of the lower wall of the cavity 43, can comprise a flexible pouch similar to a pouch of the second balancing means.

Figure 7:
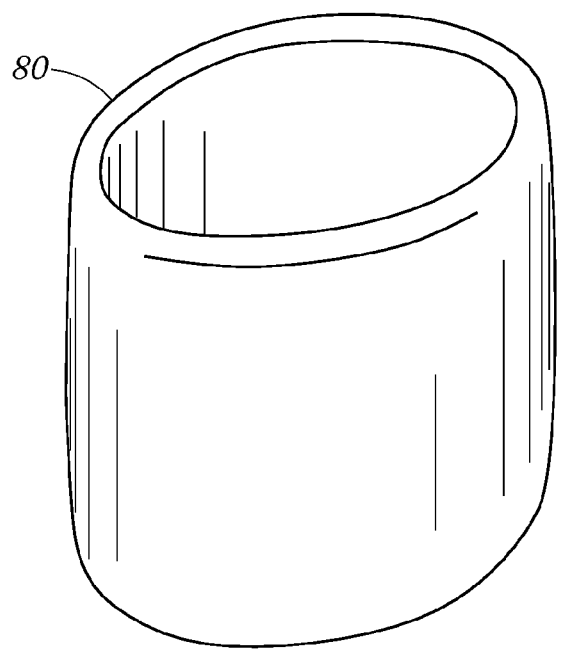
FIG. 7 is a perspective view of a second embodiment of a passive balancing unit for a separation apparatus.
Figure 8:
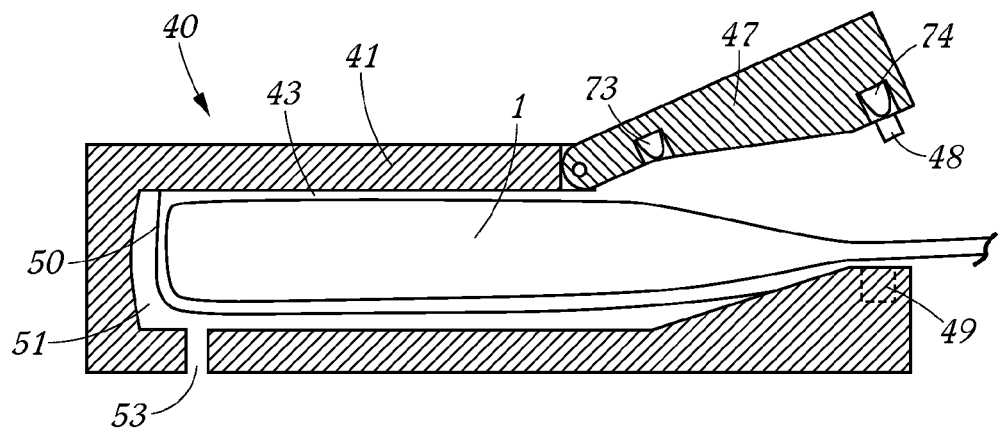
FIG. 8 is schematic view, in cross-section along a radial plane, of a separation cell of the separation apparatus of FIGS. 4 and 5.

The second balancing means, instead of comprising four interconnected pouches 81, 82, 83, 84 as shown in FIG. 6, can comprise a flexible tubular pouch 80 having two concentric walls as shown in FIG. 7. The pouch 80 is so dimensioned as to line the inner surface of the central container 34 and to have an internal volume that is larger than the volume of balancing liquid so that the balancing liquid can freely expand in one area of pouch or in another.

The pumping station 60, instead of a piston pump 61, 62, can comprise any pump (e.g. a positive displacement pump) whose output can be controlled with sufficient accuracy.

Figure 10:
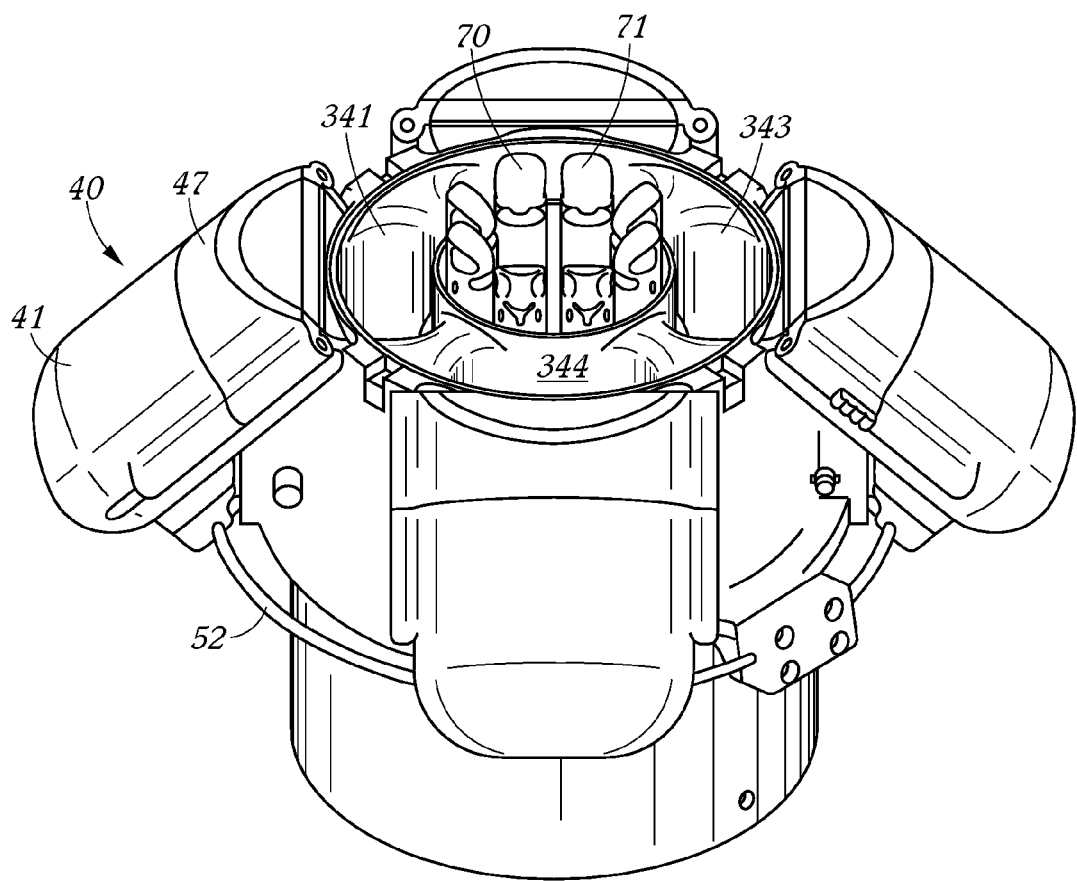
FIG. 10 is a perspective view of a rotor of a second embodiment of a separation apparatus.
Figure 11:
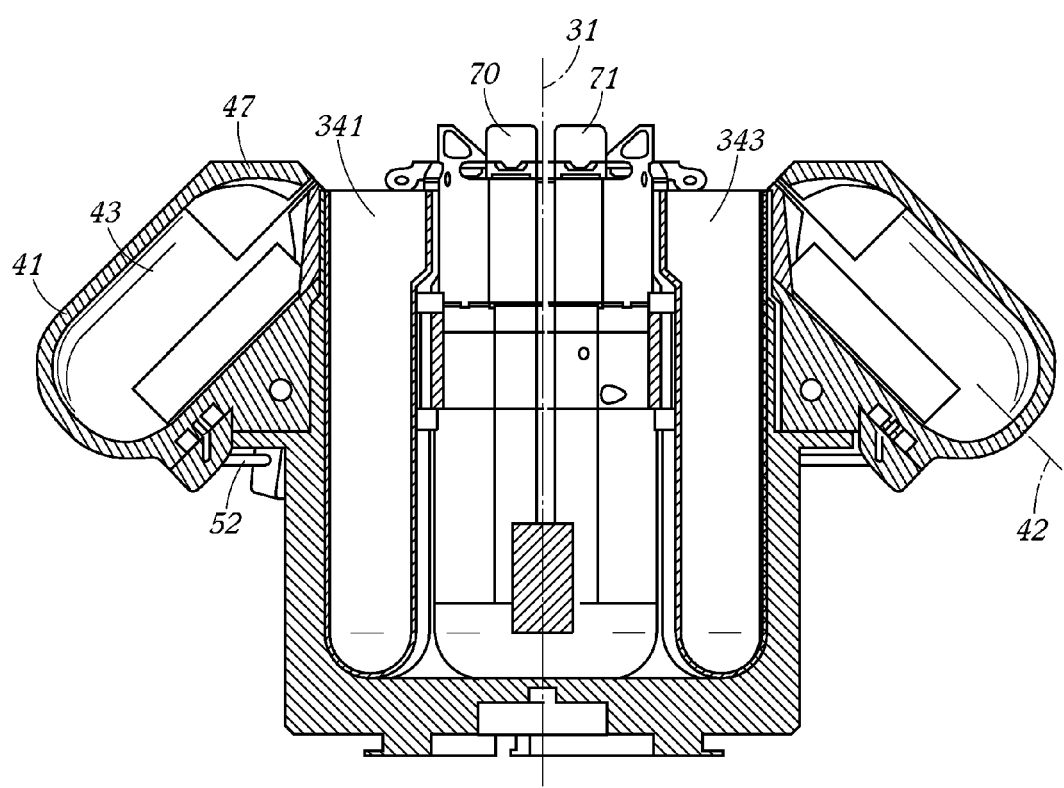
FIG. 11 is a cross-section view of the rotor of FIG. 10, along a diametral plane.
Figure 12:
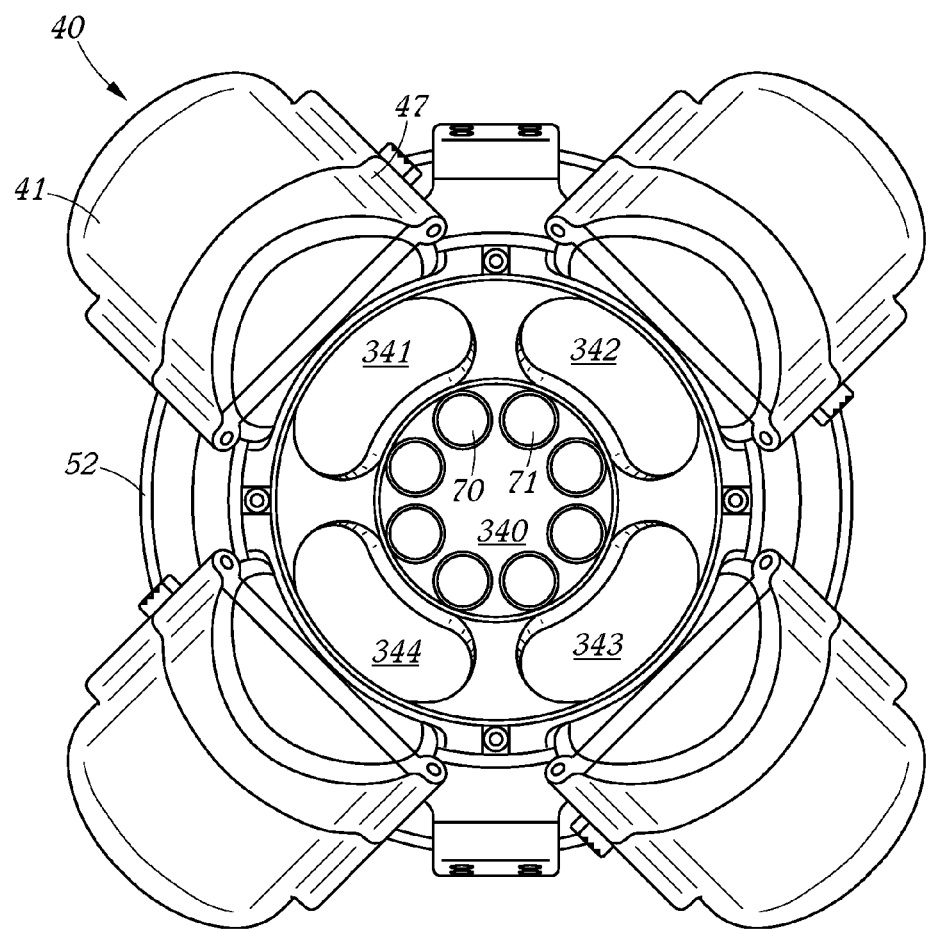
FIG. 12 is a top view of the rotor of FIG. 10.
Figure 13:
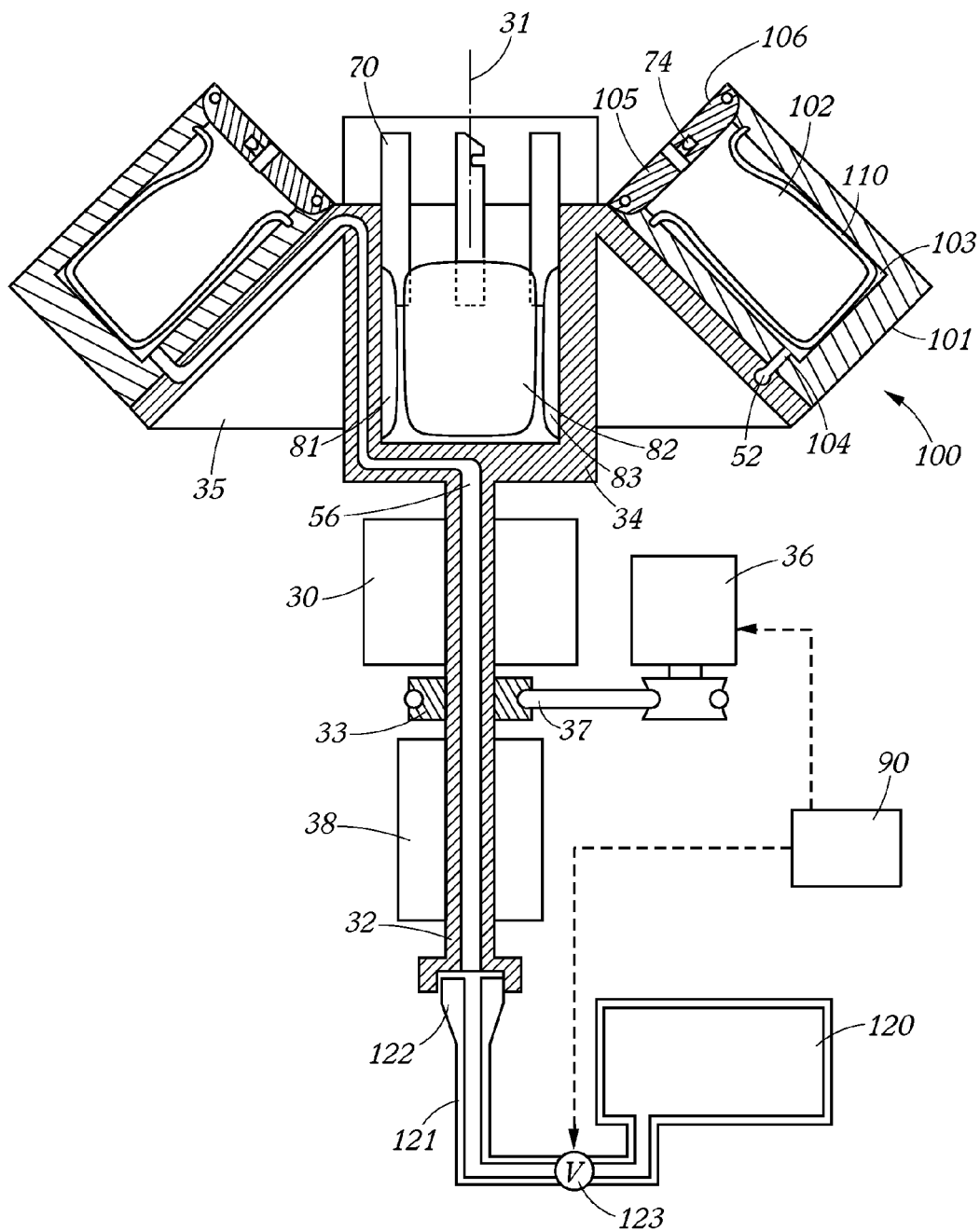
FIG. 13 is a schematic view, in cross-section along a diametral plane, of a third embodiment of a separation apparatus.
Figure 14:
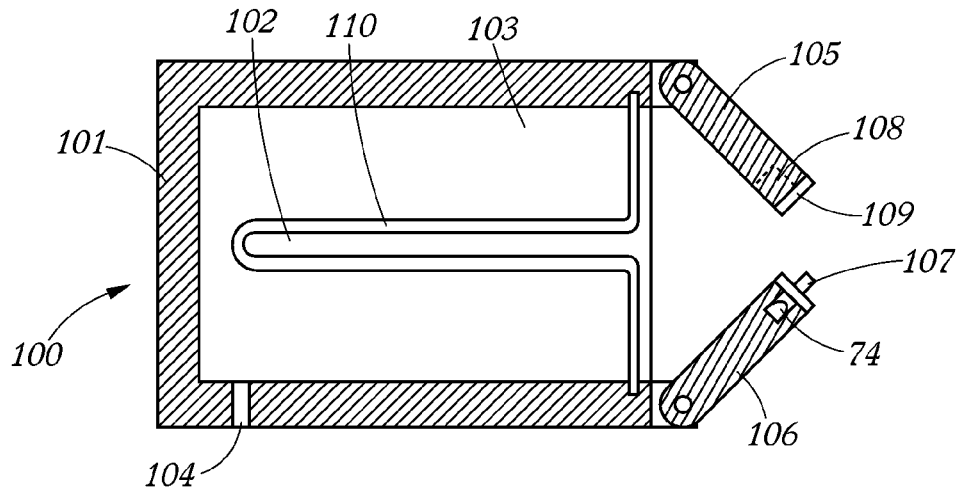
FIG. 14 is schematic view, in cross-section along a radial plane, of a separation cell of the separation apparatus of FIG. 13.

FIGS. 10, 11, 12 show the rotor of a second embodiment of a separation apparatus for four discrete volumes of a composite liquid.

The rotor of this second embodiment essentially differs from the rotor of the embodiment of FIGS. 4 and 5 in the spatial arrangement of the pinch valve members 70, 71 and of the storage means for the satellite bags with respect to the separation cells 40. In this embodiment, the storage means, instead of comprising a central container, comprises four satellite containers 341, 342, 343, 344 that are arranged around a central cylindrical cavity 340, in which the four pairs of pinch valve member 70, 71 are mounted with their longitudinal axes parallel to the rotation axis 31. The cavity 43 of a satellite container 341, 342, 343, 344 has a regular bean-like cross-section, and a central longitudinal axis that is parallel to the rotation axis 31 and intersects the longitudinal axis 42 of the associated separation cell 40.

When a set of bag as shown in FIGS. 2, 3a, 3b is mounted on the rotor of FIGS. 11 to 12, the separation bag 1 and the satellite bags 2, 3, 15 are located beyond the associated pinch valves members 70, 71 with respect to the rotation axis 31. The tubes 4, 17, 18 and the three-way connector 16, 16a, 16b connecting the bags are then in the position shown in FIGS. 2, 3a, 3b.

The operation of the separation apparatus of FIGS. 3 and 4, in accordance to a first and second an illustrative separation protocols, will be described now.

According to a first separation protocol, four discrete volumes of blood are separated into a plasma component, a first cell component comprising platelets, white blood cells, some red blood cells and a small volume of plasma (later the "buffy coat" component) and a second cell component mainly comprising red blood cells. Each volume of blood is contained in a separation bag 1 of a bag set represented in FIG. 2, in which it has previously been collected from a donor using the collection tube 5. After the blood collection, the collection tube 5 has been sealed and cut close to the separation bag. Typically, the volumes of blood are not the same in the four separation bags 1, and the hematocrit varies from one separation bag 1 to another one. Consequently, the separation bags 1 have slightly different weights.

First stage (first protocol): setting the four bag sets in the separation apparatus Four separation bags 1 are loaded into the four separation cells 40. The lids 47 are closed and locked, whereby the separation bags 1 are secured by their upper edge to the containers 41 (the pins 48 of the securing means pass then through the holes 8 in the upper corner of the separation bags 1 and engage the recesses 49 or the securing means).

The tubes 17 connecting the separations bags 1 to the plasma component bags 2, through the T connectors 16, are inserted in the groove 72 of the first pinch valve members 70. The tubes 18 connecting the separations bags 1 to the buffy coat component bags 15, through the T connector 16, are inserted in the groove 72 of the second pinch valve members 71. The four plasma component bags 2, the four buffy coat component bags 15, the four red blood cell component bags 3 and the four leuko-reduction filters 13 are inserted in the central compartment 34 of the rotor. The four plasma component bags 2 are respectively placed in direct contact with the pouches 81 to 84 of the second balancing means. The pinch valve members 70, 71 are closed and the breakable stoppers 9 in the tubes 4 connecting the separation bags 1 to the T connectors 16 are manually broken.

Second Stage (First Protocol): Balancing the Rotor in Order to Compensate for the Difference in Weights of the Separation Bags At the onset of the second stage, all the pinch valve members 70, 71 are closed. The rotor is set in motion by the centrifuge motor 36 and its rotation speed increases steadily until it rotates at a first centrifugation speed. The pumping station 60 is actuated so as to pump a predetermined overall volume of hydraulic liquid into the four hydraulic chambers 51, at a constant flow rate. This overall volume of liquid is predetermined taking into account the maximum variation of weight between blood donations, so that, at the end of the second stage, the weights in the various separation cells 40 are substantially equal and the rotor is substantially balanced, whatever the specific weights of the separation bags 1 that are loaded in the separation cells 40. Note that this does not imply that the internal cavity 43 of the separation cells 40 should be filled up at the end of the balancing stage. For the purpose of balancing the rotor, it suffices that there is enough hydraulic liquid in the separation cells 40 for equalizing the weights therein, and it does not matter if an empty space remains in each separation cell 40 (the size of this empty space essentially depends on the volume of the internal cavity 43 of a separation cell 40 and the average volume of a blood donation). Because the hydraulic chambers 51 are interconnected, the distribution of the overall volume of hydraulic liquid between the separations chambers 40 simply results from the rotation of the rotor. When the weights of the separation bags 1 are the same, the distribution of the hydraulic liquid is even. When they are not, the distribution of the hydraulic liquid is uneven, and the smaller the weight of a specific separation bag 1, the larger the volume of the hydraulic fluid in the associated hydraulic chamber 51.

Third Stage (First Protocol): the Blood Within the Separation Bags 1 is Sedimented to a Desired Level.

At the onset of this stage, all pinch valve members 70, 71 are closed. The rotor is rotated at a second centrifugation speed (high sedimentation speed or "hard spin") for a predetermined period of time that is so selected that, whatever the hematocrit of the blood in the separation bags 1, the blood sediments in each of the separation bag 1 at the end of the selected period to a point where the hematocrit of the outer red blood cell layer is about 90 and the inner plasma layer does not substantially contain anymore cells, the platelets and the white blood cells forming then an intermediary layer between the red blood cell layer and the plasma layer.

Fourth Stage (First Protocol): a Plasma Component is Transferred into the Plasma Component Bags 2.

At the onset of this stage, the rotation speed is decreased to a third centrifugation speed, the four first pinch valve members 70 controlling access to the plasma component bags 2 are opened, and the pumping station 60 is actuated so as to pump hydraulic liquid at a first constant flow rate into the hydraulic chambers 51 and consequently squeeze the separation bags 1 and cause the transfer of plasma into the plasma component bags 2.

When blood cells are detected by the bag sensor 73 in the separation cell 40 in which this detection occurs first, the pumping station 60 is stopped and the corresponding first pinch valve member 70 is closed, either immediately or after a predetermined amount of time selected in view of the volume of plasma that it is desirable in the buffy coat component to be expressed in a next stage.

Following the closure of the first (first) pinch valve member 70 (i.e. the first pinch valve of the group of first pinch valve members 70) to close, the pumping station 60 is actuated anew so as to pump hydraulic liquid at a second, lower, flow rate into the hydraulic chambers 51 and consequently squeeze the three separation bags 1 whose outlet is not closed by the corresponding first pinch valve members 70.

When blood cells are detected by the bag sensor 73 in the separation cell 40 in which this detection occurs second, the pumping station 60 is stopped and the corresponding first pinch valve member 70 is closed (same timing as for the closing of the first (first) pinch valve member to close).

Following the closure of the second (first) pinch valve member 70 to close, the pumping station 60 is actuated anew so as to pump hydraulic liquid at the second flow rate into the hydraulic chambers 51 and consequently squeeze the two separation bags 1 whose outlet is not closed by the corresponding first pinch valve members 70.

When blood cells are detected by the bag sensor 73 in the separation cell 40 in which this detection occurs third, the pumping station 60 is stopped and the corresponding first pinch valve member 70 is closed (same timing as for the closing of the first (first) pinch valve member to close).

Following the closure of the third (first) pinch valve member 70 to close, the pumping station 60 is actuated anew so as to pump hydraulic liquid at the second flow rate into the hydraulic chambers 51 and consequently squeeze the separation bag 1 whose outlet is not yet closed by the corresponding first pinch valve member 70.

When blood cells are detected by the bag sensor 73 in the separation cell 40 in which this detection occurs last, the pumping station 60 is stopped and the corresponding first pinch valve member 70 is closed (same timing as for the closing of the first pinch valve member to close).

In the plasma component transfer process described above, the transfer of the four plasma components starts at the same time, run in part simultaneously and stop independently of each other upon the occurrence of a specific event in each separation bag (detection of blood cells by the bag sensor).

As a variant, when the second flow rate is sufficiently low and the closing of the first pinch valve member 70 occurs almost simultaneously with the detection of blood cells in the separation bags, then the pumping station can be continuously actuated during the fourth stage.

The fourth stage ends when the four first pinch valve members 70 are closed.

Fifth Stage (First Protocol): a Buffy Coat Component is Transferred into the Buffy Coat Component Bags 15.

The control unit 90 is programmed to start the fifth stage after the four first pinch valve members 70 are closed, upon receiving information from the last bag sensor 73 to detect blood cells.

At the onset of this stage, the rotation speed remains the same (third centrifugation speed), a first of the four second pinch valve members 71 controlling access to the buffy coat component bags 15 is opened, and the pumping station 60 is actuated so as to pump hydraulic liquid at a third constant flow rate into the hydraulic chambers 51 and consequently squeeze the separation bag 1 in the separation cell 40 associated with the opened second pinch valve members 71 and cause the transfer of the buffy coat component into the buffy coat component bag 2 connected to this separation bag 1.

After a predetermined period of time after blood cells are detected by the tube sensor 74 in the separation cell 40 associated with the opened second pinch valve member 71, the pumping station 60 is stopped and the second pinch valve member 71 is closed.

After the first (second) pinch valve member 71 has closed (i.e. the first pinch valve of the group of second pinch valve members 71), a second (second) pinch valve member 71 is opened, and a second buffy coat component is transferred into a buffy coat component bag 2, in the same way as above.

The same process is successively carried out to transfer the buffy coat component from the two remaining separation bags 1 into the buffy coat component bag 2 connected thereto.

In the buffy coat component transfer process described above, the transfers of the four buffy coat components are successive, and the order of succession is predetermined. However, each of the second, third and four transfers starts following the occurrence of a specific event at the end of the previous transfer (detection of blood cells by the tube sensor 74 or closing of the second valve member 71).

As a variant, when the third flow rate is sufficiently low and the closing of the second pinch valve members 71 occurs almost simultaneously with the detection of blood cells in the tubes 4, then the pumping station can be actuated continuously during the fourth stage.

As a variant, the control unit 90 is programmed to start the fifth stage after a predetermined period of time after receiving information from the first (or the second or the third) bag sensor 73 to detect blood cells. The period of time is statistically or empirically determined so that, whatever the event from which it starts running (detection of the blood cells by either one of the first, second, and third bag sensor 73 to detect blood cells), the four first pinch valve members 70 are closed when it is over.

The fifth stage ends when the four second pinch valve members 71 are closed.

Sixth Stage (First Protocol): the Centrifugation Process is Ended.

The control unit 90 is programmed to start the sixth stage after the four (second) pinch valve members 71 are closed, upon receiving information from the last tube sensor 74 to detect blood cells.

The rotation speed of the rotor is decreased until the rotor stops, the pumping station 60 is actuated so as to pump the hydraulic liquid from the hydraulic chambers 51 at a high flow rate until the hydraulic chambers 51 are empty, and the first and second pinch valve members 70, 71 are actuated so as to seal and cut the tubes 17, 18. The blood cells remain in the separation bags 1.

When the fifth stage is completed, the four bag sets are removed from the separation apparatus and each bag set is separately handled manually.

The breakable stopper 10 blocking the communication between the separation bag 1 and the tube 6 connected thereto is broken, as well as the breakable stopper 14 blocking the communication between the second satellite bag 3 and the tube 6. The storage solution contained in the second satellite bag 3 is allowed to flow by gravity through the leuko-reduction filter 13 and into the separation bag 1, where it is mixed with the red blood cells so as to lower the viscosity thereof. The content of the separation bag 1 is then allowed to flow by gravity through the filter 13 and into the second satellite bag 3. The white blood cells are trapped by the filter 13, so that substantially only red blood cells are collected into the second satellite bag 3.

As a variant, the control unit 90 is programmed to start the sixth stage after a predetermined period of time after receiving information from the first (or the second or the third) tube sensor 74 to detect blood cells. The period of time is statistically or empirically determined so that, whatever the event from which it starts running (detection of the blood cells by either one of the first, second, and third tube sensor 74 to detect blood cells), the four second pinch valve members 71 are closed when it is over.

According to a second separation protocol, four discrete volumes of blood are separated into a plasma component, a platelet component and a red blood cell component. Each volume of blood is contained in a separation bag 1 of a bag set represented in FIG. 2, in which it has previously been collected from a donor using the collection tube 5. After the blood collection, the collection tube 5 has been sealed and cut close to the separation bag 1. Typically, the volumes of blood are not the same in the four separation bags 1, which, consequently, have slightly different weights. Also, typically, the hematocrit varies from one separation bag 1 to another one.

First stage (second protocol): setting the four bag sets in the separation apparatus This stage is identical to the first stage of the first protocol.

Second stage (second protocol): balancing the rotor in order to compensate for the difference in weights of the separation bags This stage is identical to the second stage of the first protocol.

Third stage (second protocol): the blood within the separation bags 1 is sedimented to a desired level.

This stage is identical to the third stage of the first protocol.

Fourth stage (second protocol): a first, larger, portion of plasma is transferred into the plasma bags 2, while a second, smaller, portion of plasma remains in the separation bags 1. This stage is substantially the same as the fourth stage of the first protocol. However, the expression of plasma from each separation bag 1 into the attached plasma component bag 2 is stopped immediately after detection of blood cells by the corresponding bag sensor 73, so that the volume of plasma remaining in the separation bag 1 is large enough to allow the platelets to be re-suspended therein.

Fifth stage (second protocol): a platelet component is prepared in the separation bag 1.

At the onset of this fifth stage, the first and second valve members 70, 71 are closed. The rotor is stopped and the pumping station 60 is actuated so as to pump a volume of hydraulic liquid from the hydraulic chambers 51 at a high flow rate. The rotor is then controlled so as to oscillate back and forth around the rotation axis 31 for a determined period of time, at the end of which the cells in the separation bags 1 are substantially suspended in plasma. The rotor is then set in motion again by the centrifuge motor 36 so that its rotation speed increases steadily until it reaches a fourth centrifugation speed (low sedimentation speed or "soft spin"). The rotor is rotated at the fourth rotation speed for a predetermined period of time that is selected so that the blood sediments in the separation bags 1 at the end of the selected period to a point where the separation bags 1 exhibit an outer layer comprising packed red blood cells and an inner annular layer substantially comprising platelets suspended in plasma.

Sixth stage (second protocol): a platelet component is transferred into the platelet bags 15. This stage is substantially the same as the fifth stage of the first protocol (buffy coat expression).

Seventh stage (second protocol): the centrifugation process is ended.

This stage is substantially the same as the sixth stage of the first protocol.

FIGS. 13 to 18 show a third embodiment of a separation apparatus for four discrete volumes of a composite liquid.

The separation apparatus of FIG. 13 to 18 is particularly adapted to the separation of a composite fluid in two components, for example the separation of whole blood into a cell component (red blood cells, white cells and platelets) and a plasma component substantially devoid of cells or the separation of whole blood into a cell component (red blood cells, white cells and a small amount of platelets) and a plasma component containing a large amount of platelets in suspension.

The main differences between the first separation apparatus shown in FIGS. 4 and 5 and the third separation apparatus shown in FIGS. 13 to 18 are as follows. The shape of the separation cells 100 of the third separation apparatus is different from the shape of the separation cells 40 of the first separation apparatus. Each of the separation cells 100 of the third separation apparatus is associated with one pinch valve member 70 and one tube sensor 74. The third separation apparatus does not comprise a pumping station for pumping a hydraulic liquid in and out of the hydraulic chambers of the separation cells 100.

In more details, a separation cell 100 for the third separation apparatus comprises a container 101 having the general shape of a rectangular parallelepiped. The cavity (also referred to as the "separation compartment") of the container 101, which has also the general shape of a rectangular parallelepiped, is so dimensioned as to loosely accommodate a separation bag 1 full of liquid, of the type shown in FIG. 2. The separation cell 100 further comprises an elastic diaphragm 110, which defines within the cavity of the container 101a first chamber 102 for receiving a separation bag 1, and a second hydraulic chamber 103 that is connected to the peripheral manifold 52, through an inlet aperture 104 close to the bottom of the container 101. The separation cell 100 further comprises a lid having two flaps 105, 106 that are hinged to the longer parallel sides of the opening of the container 101. The two flaps 105, 106 can be locked in a closed position by a locking means (not shown). The separation cell 100 further comprises a securing means for securing a separation bag 1 within the separation cell 100.

The bag securing means comprises two pins 107 and two corresponding recesses 108 that respectively protrude or open on the edges of the flaps 105, 106 that face each other when the lid is closed. The two pins 107 are so spaced apart and dimensioned as to fit into the two holes 8 in the upper corner of a separation bag 1. The two flaps 105, 106 also comprise on their facing edges three semi-cylindrical holes 109 for accommodating the proximal end of three tubes 4, 5, 6 embedded in the upper area of a separation bag 1. The outer flap 106 includes a cavity facing the median semi-cylindrical hole 109, for containing the bag sensor 74.

Figure 15:
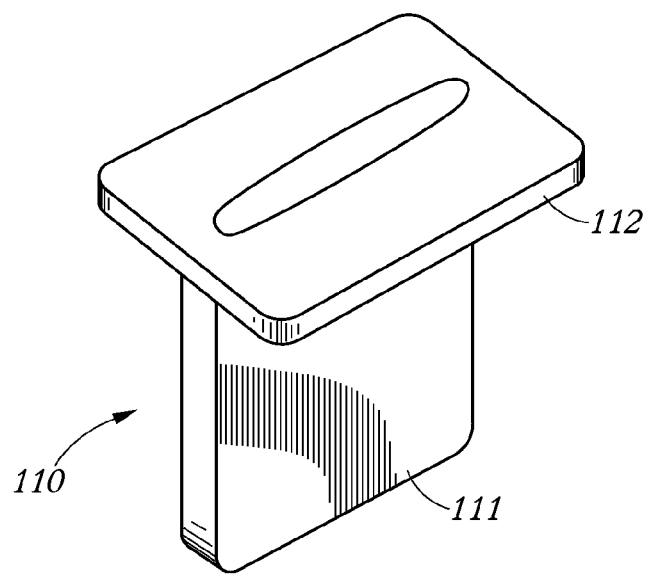
FIG. 15 is a perspective view of the flexible diaphragm of the separation cell of FIG. 14.
Figure 16:
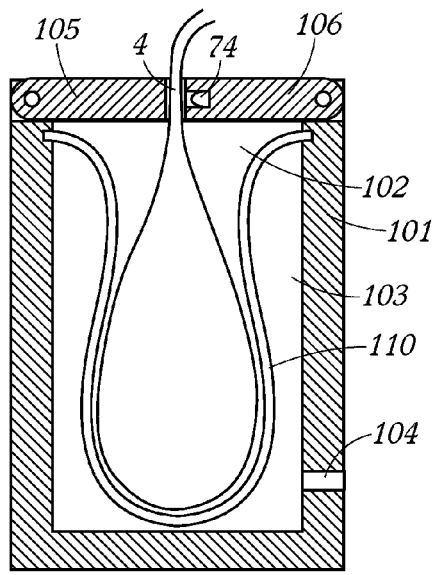
FIGS. 16 to 18 are schematic views, in cross-section along a radial plane, of the separation cell FIG. 14 containing a separation bag at different stages of a separation process.
Figure 17:
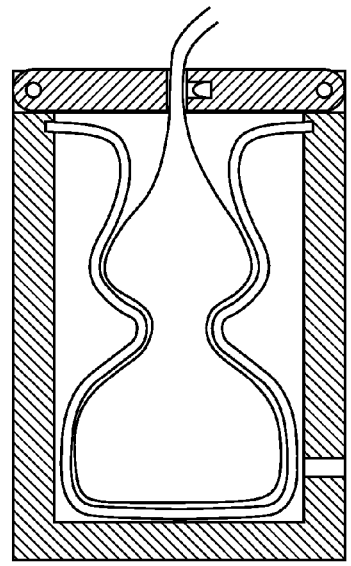
Figure 18:
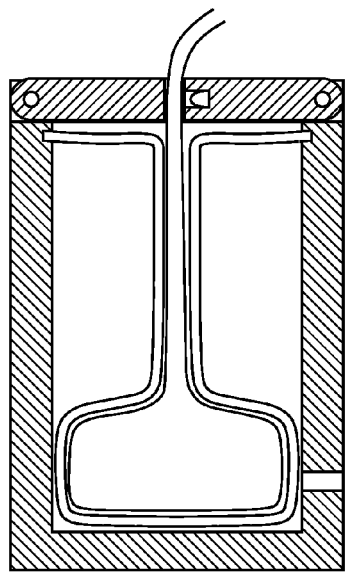

As shown in FIGS. 15 to 18, the diaphragm 110 comprises a flat rectangular socket 111 almost as wide as a separation cell 100. The diaphragm 110 further comprises a large, rectangular, connecting portion 112 extending around the mouth of the socket 111, perpendicularly to the socket 111 when the diaphragm 110 is not deformed by a separation bag 1 and it is held in an upright position (FIG. 15). The socket 111 is connected to the connecting portion 112 along the longitudinal median axis thereof. The connecting portion 112 has a surface slightly larger than a transversal cross-section of the cavity of the container 101. The diaphragm 110 is tightly attached to the top of the container 101 by a peripheral area of the connecting portion 112. The diaphragm 110 is made of an elastic and deformable elastomeric material so selected that the diaphragm 110 conforms very closely the shape of a separation bag 1 before and during centrifugation and as shown in FIGS. 16 to 18.

As mentioned above, the separation apparatus shown in FIG. 13 does not comprise a pumping station for pumping a hydraulic fluid in and out of the hydraulic chambers 103. Instead, it comprises a reservoir 120 for hydraulic liquid, which is fixed with respect to the rotor, and which is directly connected to the rotor duct 56 by a conduit 121 and a rotary seal 122. The conduit 121 is fitted with a valve 123. The reservoir 120 is secured to a frame of the separation apparatus so as to be lower than the four separation cells 100. When the separation apparatus is used for separating red blood cells from plasma (with or without suspended platelets), the density of the hydraulic liquid is selected, for reasons explained below, so as to be between the density of packed red blood cells and the density of plasma.

The component transferring means of the third separation apparatus essentially comprises the reservoir 120 that is directly connected to the rotor duct 56 by the rotary seal 122, the hydraulic chambers 103, and the motor 36 that drives the rotor in rotation. When the valve 123 is opened and the rotation speed of the rotor reaches a determined threshold, which depends on the height between the reservoir 120 and the separation cells 100 and the distance between the rotation axis 31 and the separation cells 100, then the hydraulic liquid flows from the reservoir 120 into the hydraulic chambers 103 so as to fill up the hydraulic chamber 103 and squeeze the separation bags 1 therein, whatever the volume/weight of the separation bags 1. The speed threshold is substantially below the rotation speed at which the rotor is rotated for separating blood components ("high spin" as well as "soft spin). The transfer of a separated component from a separation bag 1 into a satellite bag 2 is then controlled by the opening/closing of the pinch valve member 70 in which the tube 4 connecting the two bags is inserted.

The first balancing means of the third separation apparatus essentially comprises the reservoir 120 that is directly connected to the rotor duct 56 through the rotary seal 122, the hydraulic chambers 103, the motor 36 that drives the rotor in rotation, and the valve 123. At the onset of a separation process, the valve 123 is opened for a predetermined period of time so as to allow the transfer, in the interconnected hydraulic chambers 103, of a predetermined volume of hydraulic liquid that is so selected as to balance the rotor in the most unbalanced situation. For whole blood, the determination of this balancing volume takes into account the maximum difference in volume between two blood donations, and the maximum difference in hematocrit (i.e. in density) between two blood donations.

A variant of the third embodiment of a separation apparatus does not comprise a valve 123 on the conduit 121 connecting the reservoir 120 to the rotor duct 56. As a result, when the threshold speed is reached, the hydraulic liquid is pumped from the reservoir 120 into the hydraulic chambers 103 until the pressure that is building up within the separation cells 100 prevents further pumping. The filling up of the space available in the separation cells 100 with hydraulic liquid might not however result in an optimal balance of the rotor depending, in particular, on the difference in weight of the separation bags 1, of their volume, and of the density of the hydraulic liquid.

The operation of the third separation apparatus, in accordance to a third illustrative separation protocol, will be described now.

According to a third separation protocol, four discrete volumes of blood are separated into a plasma component (including or not including a substantial amount of platelets) and a blood cell component (including platelets, or residual platelets, white blood cells and red blood cells). Each volume of blood is contained in a separation bag 1 of a bag set represented in FIG. 1, in which it has previously been collected from a donor using the collection tube 5. After the blood collection, the collection tube 5 has been sealed and cut close to the separation bag 1. Typically, the volumes of blood are not the same in the four separation bags 1 and the hematocrit varies from one separation bag 1 to another one. As a result, the separation bags have slightly different weights.

First stage (third protocol): setting the four bag sets in the separation apparatus Four separation bags 1 are inserted into the socket 111 of a diaphragm 110 within the four separation cells 100 as shown in FIG. 16. The two flaps 105, 106 of the lids of the separation cells 100 are closed and consequently secure the top of the separation bags 1 to the separation cells 100. The tube sensors 74 embedded in the outer flap 106 of the lids now face the proximal end of the tubes 4 connecting the separation bags 1 to the plasma component bags 2. The tubes 4 are inserted in the groove 72 of the pinch valve members 70. The four plasma component bags 2, the four red blood cell component bags 3 and the four leuko-reduction filters 13 are inserted in the central compartment 34 of the rotor. The pinch valve members 70 are closed and the breakable stoppers 9 in the tubes 4 connected to the plasma component bags 2 are manually broken.

Second Stage (Third Protocol): Balancing the Rotor in Order to Compensate for the Difference in Weights of the Separation Bags At the onset of this second stage, the pinch valve members 70, in which the tubes 4 are engaged, are closed. The valve 123 on the conduit connecting the reservoir 120 to the rotor duct 56 is opened. The rotor is set in motion by the centrifuge motor 36 and its rotation speed increases steadily until it rotates at a predetermined sedimentation speed. Before it rotates at the sedimentation speed, the rotor reaches a threshold speed at which its rotation causes the pumping of hydraulic liquid from the reservoir 120 into the interconnected hydraulic chambers 103 of the separation cells 100. The valve is closed 123 after a predetermined amount of hydraulic fluid sufficient for balancing the rotor has been transferred in the hydraulic chambers 103. Because the hydraulic chambers 103 are interconnected by the peripheral manifold 52, the hydraulic liquid gets automatically distributed in the separation cells 100 so as to balance the rotor. When the weights of the separation bags 1 are the same, the distribution of the hydraulic liquid is even. When they are not, the distribution of the hydraulic liquid is uneven, and the smaller the weight of blood in a specific separation bag 1, the larger the volume of the hydraulic fluid in the associated hydraulic chamber 103.

Third Stage (Third Protocol): the Blood Within the Separation Bags 1 is Sedimented to a Desired Level.

When it is desired to separate a plasma component containing a large amount of suspended platelets ("platelet rich plasma") and a cell component mainly containing red blood cells and white blood cells, the rotor is rotated at a first sedimentation speed (about 2000 RPM, usually referred to as "soft spin").

When it is desired to separate a plasma component substantially devoid of cells ("platelet poor plasma") and a cell component containing red blood cells, white blood cells and platelets, the rotor is rotated at a second sedimentation speed (about 3200 RPM, usually referred to as "hard spin").

The rotor is rotated at the selected sedimentation speed for a predetermined period of time that is selected so that, whatever the hematocrit of the blood in the separation bags 1, the blood sediments at the desired level in each of the separation bag 1 at the end of the selected period. Since, as mentioned above, the density of the hydraulic liquid is selected so as to be between the density of the packed red cells and the density of the plasma, the separation bag 1 will take a hour-glass shape at the end of the sedimentation stage, as shown in FIG. 17.

Fourth Stage (Third Protocol): a Plasma Component is Transferred into the Satellite Bags 2.

At the onset of this stage, the four pinch valve members 70 controlling the access to the plasma component bags 2 are opened. This causes a decrease in pressure within the separation cells 100 and hydraulic liquid starts flowing again into the hydraulic chambers 103. The raising volume of hydraulic fluid in the hydraulic chamber 103 squeezes the separation bags 1 and causes the transfer of the plasma component into the first satellite bags 2. Because the hydraulic liquid has a lower density than the density of the packed red blood cells, the red blood cells remain at the bottom of the separation cell 100 and the separation bags 1 progressively collapse above the red cells as shown in FIG. 18.

When each tube sensor 74 detects blood cells, then the associated pinch valve member 70 is closed. When the volumes of blood in the four separation bags 1 are different, and/or the hematocrit of the blood in the four separation bags 1 is different (which will be generally the case), then the four pinch valve members 70 close one after the other.

The fourth stage end when the four pinch valve members 70 are closed.

Fifth Stage (Third Protocol): the Centrifugation Process is Ended.

When the last pinch valve member 70 closes, the rotation speed of the rotor is decreased until the rotor stops. The hydraulic liquid simultaneously drains from the hydraulic chambers 103 into the reservoir 120. The red blood cells and the white blood cells remain in the separation bag 1 (as well as the platelets when the plasma component collected is a "platelet poor plasma").

When the fifth stage is completed, the four bag sets are removed from the separation apparatus and each bag set is separately handled manually.

The breakable stopper 10 blocking the communication between the separation bag 1 and the tube 6 connected thereto is broken, as well as the breakable stopper 14 blocking the communication between the second satellite bag 3 and the tube 6. The storage solution contained in the second satellite bag 3 is allowed to flow by gravity through the filter 13 and into the separation bag 1, where it is mixed with the blood cells so as to lower the viscosity thereof. The content of the separation bag 1 is then allowed to flow by gravity through the filter 13 and into the second satellite bag 3. The white blood cells and the platelets are trapped by the filter 13, so that substantially only red blood cells are collected into the second satellite bag 3.

Figure 19:
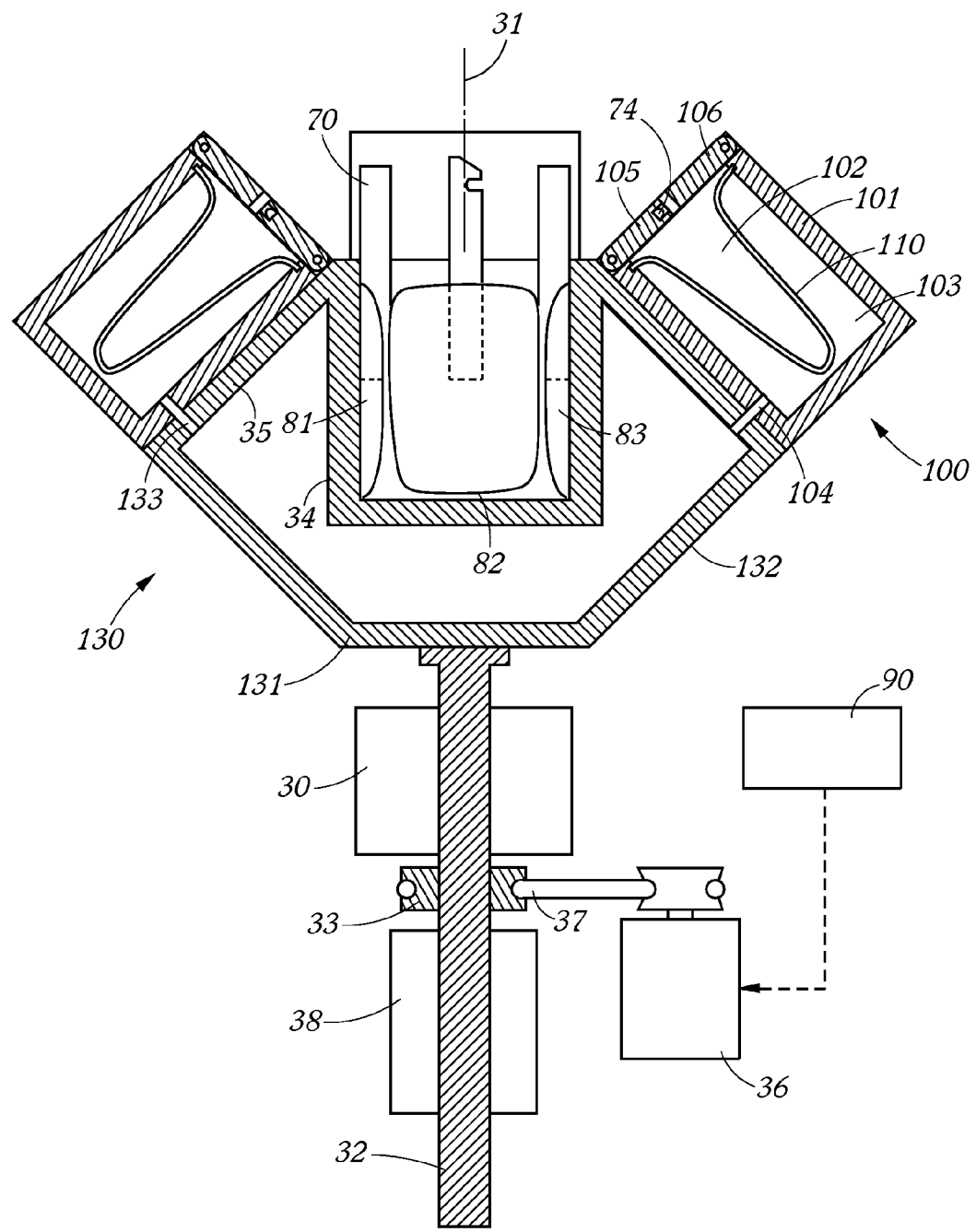
FIG. 19 is a schematic view, in cross-section along a diametral plane, of a fourth embodiment of a separation apparatus.

FIG. 19 shows a fourth embodiment of a separation apparatus for four discrete volumes of a composite liquid.

The main differences between the third separation apparatus shown in FIGS. 13 to 18 and the fourth separation apparatus shown in FIG. 19 are as follows. The fourth separation apparatus does not comprise a fixed reservoir directly connected to the separation chambers, via a conduit, a rotary seal and a rotor duct. The fourth separation apparatus comprises a hydraulic liquid reservoir 130 that is mounted on the rotor.

The rotor of the apparatus of FIG. 19 comprises a central container 34 for satellite bags, having the shape of a cylindrical bucket; a turntable 35 having a frusto-conical wall supporting four separation cells 100 at an angle with respect to the rotation axis 31; the turntable 35 is connected by its smaller diameter section to an upper rim of the central container 34 so as to flare underneath the rim of the central container 34; a reservoir 130 for hydraulic liquid, which comprises a circular bottom wall 131 and frusto-conical wall 132 connected by its smaller diameter section to the circular bottom wall 131 and by its larger diameter section to the lower rim of the turntable 35 (i.e. the section of the turntable having the larger diameter). In other words, the interior of the reservoir 130 has a complex geometrical volume that is symmetrical with respect to the rotation axis 31 and that is defined by the outside surface or the central container 34, the inner surface of the turntable 35, the inner surface of the frusto-conical wall 132 of the reservoir, and the inner surface of the bottom wall 131 of the reservoir. A rotor shaft 32 is connected to the bottom wall of the reservoir 130.

The reservoir 130 is fluidly connected to the hydraulic chamber 103 of each separation cell 100 by an outlet aperture 133 through the turntable 35 that coincides with the inlet aperture 104 of the hydraulic chambers 103. As shown, the outlet apertures 133 are located the farthest from the rotation axis 31. With this arrangement, the hydraulic liquid flows from the reservoir 130 into the hydraulic chambers 103 of the separation cells 100 under centrifugal forces as soon as the rotor starts rotating. When the separation apparatus is to be used for separating red blood cells from plasma (with or without suspended platelets), the density of the hydraulic fluid is selected so as to be between the density of pack red cells and the density of plasma.

In this fourth embodiment of a separation apparatus, the component transferring means essentially comprise the reservoir 130, the hydraulic chambers 103 and the motor 36 that drives the rotor in rotation. When the rotor rotates, the hydraulic liquid drains from the reservoir 130 into the hydraulic chambers 103 under centrifugal forces and presses the separation bags 1 within the separation cell 100 through the elastic diaphragm 110. The transfer of a separated component from a separation bag 1 into a satellite bag 2 is controlled by the opening/closing of the pinch valve member 70 in which the tube 4 connecting the two bags is inserted.

The first balancing means essentially comprise the reservoir 130, the hydraulic chambers 103 and the motor 36 that drives the rotor in rotation. As soon as the rotor starts rotating, hydraulic fluid flows from the reservoir 130 into the hydraulic chambers 103 until it completely fills up the space let vacant in the separation cells 100 by the separation bags 1, which happens before the rotor has reach the desired sedimentation speed. The filling up of the space available in the separation cells 100 with hydraulic liquid might not however result in an optimal balance of the rotor depending, in particular, on the difference in weight of the separation bags 1, on their volume, and on the density of the hydraulic liquid.

It will be apparent to those skilled in the art that various modifications can be made to the apparatus and method described herein. Thus, it should be understood that the invention is not limited to the subject matter discussed in the specification. Rather, the present invention is intended to cover modifications and variations.

The invention claimed is:

1. A centrifuge comprising
a rotor;
more than one container on the rotor;
a composite fluid chamber in each container on the rotor adapted to receive a composite fluid;
a balancing assembly comprising
a source of hydraulic liquid;
a rotor duct in the rotor directly connected to the source of hydraulic liquid;
an hydraulic chamber in each container on the rotor wherein the hydraulic chambers are interconnected and are connected to the rotor duct; and
a motor for rotating the rotor wherein rotation of the rotor causes hydraulic liquid to be transferred from the source to the interconnected hydraulic chambers to balance any unbalance in the rotor due to differences in the composite fluid.

2. The centrifuge of claim 1 further comprising an openable valve between the source of hydraulic liquid and the rotor duct to control the transfer of the hydraulic liquid.

3. The centrifuge of claim 1 further comprising a rotary seal on the rotor to permit distribution of the hydraulic liquid during rotation of the rotor.

4. The centrifuge of claim 1 wherein the source of hydraulic liquid is a reservoir mounted on the rotor.

5. The centrifuge assembly of claim 4 wherein the reservoir defines an internal volume that is symmetrical with respect to the rotation axis of the rotor.

6. The centrifuge of claim 1 further comprising an elastic socket in each container on the rotor wherein the hydraulic chamber is on one side of the elastic socket.

7. The centrifuge of claim 6 wherein the elastic socket is secured to the container to extend between at least two walls of the container.

8. A method of separating discrete volumes of a composite fluid comprising
providing a centrifuge having a rotor and more than one container on the rotor wherein each container contains a hydraulic chamber and a composite fluid chamber adapted to receive a composite fluid;
interconnecting the hydraulic chambers;
rotating the rotor and the containers on the rotor;
separating the discrete volumes of the composite fluid during the rotating step;
transferring a volume of hydraulic liquid into the interconnected hydraulic chambers to balance the centrifuge comprising
connecting a source of hydraulic liquid to the interconnected hydraulic chambers, and
distributing by the rotation of the rotor the hydraulic liquid from the source to the interconnected hydraulic chambers.

9. The method of claim 8 wherein the transferring step further comprises
opening a valve between the source of hydraulic liquid and the interconnected hydraulic chambers.

10. The method of claim 8 wherein the distributing step comprises distributing hydraulic liquid from the source through a duct in the rotor to the interconnected hydraulic chambers.

11. The method of claim 8 wherein the source of hydraulic liquid is a reservoir mounted on the rotor and the distributing step comprises distributing the hydraulic liquid from the reservoir to the interconnected hydraulic chambers.

12. The method of claim 8 wherein the distributing step comprises distributing the hydraulic liquid from the source through a rotary seal to the interconnected hydraulic chambers.

* * * * *